(12) United States Patent
Vettermann

(10) Patent No.: US 10,047,138 B1
(45) Date of Patent: Aug. 14, 2018

(54) FUSION PROTEIN, CELLS EXPRESSING THE FUSION PROTEIN, AND USES THEREOF

(71) Applicant: AMGEN INC., Thousand Oaks, CA (US)

(72) Inventor: Christian Vettermann, Berkeley, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 14/956,787

(22) Filed: Dec. 2, 2015

Related U.S. Application Data

(60) Provisional application No. 62/086,783, filed on Dec. 3, 2014.

(51) Int. Cl.
  *C07K 14/725* (2006.01)
  *C07K 14/705* (2006.01)
  *G01N 33/68* (2006.01)

(52) U.S. Cl.
  CPC ........ *C07K 14/7051* (2013.01); *C07K 14/705* (2013.01); *G01N 33/6869* (2013.01); *G01N 2333/55* (2013.01)

(58) Field of Classification Search
  None
  See application file for complete search history.

(56) References Cited

U.S. PATENT DOCUMENTS

2003/0105000 A1* 6/2003 Pero ........................ A61K 38/06
  514/19.3
2006/0247191 A1* 11/2006 Finney ............. C07K 14/70503
  514/44 R

OTHER PUBLICATIONS

Chen and Flies (Nat. Rev. Immunol. Apr. 2013 13(4): 227-242).*
Rudikoff et al. (PNAS USA, 1982, 79: 1979-1983).*
Burgess et al. (J of Cell Bio. 111:2129-2138, 1990).*
Ibragimova and Wade (Biophysical Journal, Oct. 1999, vol. 77, pp. 2191-2198).*
Call et al., The structure of the zetazeta transmembrane dimer reveals features essential for its assembly with the T cell receptor. *Cell*, 127(2): 355-68 (2006).
Chattopadhyay et al., Sequence, structure, function, immunity: structural genomics of costimulation. *Immunol. Rev.* 229(1): 356-86 (2009).
Chattopadhyay et al., Structural basis of inducible costimulator ligand costimulatory function: determination of the cell surface oligomeric state and functional mapping of the receptor binding site of the protein. *J. Immunol.* 177: 3920-9 (2006).
Chen et al., Novel approach to generate genetically engineered, sortable, ANGFR-tagged mouse Th17 cells. *Cell. Biochem. Biophys.* 64: 233-40 (2012).
Kow et al., Costimulatory pathways: Physiology and potential therapeutic manipulation in systemic lupus erythematosus. *Clin. Dev. Immunol.* Article ID 245928: 1-12 (2013).
Krogh et al., Predicting transmembrane protein topology with a hidden Markov model: application to complete genomes. *J. Mol. Biol.* 305: 567-80 (2001).
Kuhns et al., Piecing together the family portrait of TCR-CD3 complexes. *Immunol. Rev.* 250: 120-43 (2012).
Lindsey et al., CD69 expression as an index of T-cell function: assay standardization, validation and use in monitoring immune recovery. Cytotherapy, <http://www.ncbi.nlm.nih.gov/pubmed/17453964.> 9(2): 123-32 (2007).
Menne et al., A comparison of signal sequence prediction methods using a test set of signal peptides. *Bioinformatics*, 16(8): 741-2 (2000).
Rabinowitz et al., Altered T cell receptor ligands trigger a subset of early T cell signals. *Immunity*, 5(2): 125-35 (1996).
Rutledge et al., Transmembrane helical interactions: zeta chain dimerization and functional association with the T cell antigen receptor. *EMBO J.* 11(9): 3245-54 (1992).
Song et al., Intracellular signals of T cell costimulation. *Cell. Mol. Biol.* 5(4): 239-47 (2008).
Verhoeyen et al., Lentiviral Vector Gene Transfer into Human T Cells, in Genetic Modification of Hematopoietic Stem Cells, Methods in Molecular BiologyTM, vol. 508, pp. 97-114 (2009).
Wilson et al., B7RP-1-ICOS interactions are required for optimal infection-induced expansion of CD4+ Th1 and Th2 responses. *J. Immunol.* 177(4): 2365-72 (2006).
Yong et al., The role of costimulation in antibody deficiencies: ICOS and common variable immunodeficiency. *Immunol. Rev.* 229: 101-13 (2009).
Zhang et al., Oncogenic tyrosine kinase NPM-ALK induces expression of the growth-promoting receptor ICOS. *Blood*, 118(11): 3062-71 (2011).

* cited by examiner

*Primary Examiner* — Peter J Reddig
(74) *Attorney, Agent, or Firm* — Marshall, Gerstein & Borun LLP

(57) ABSTRACT

Described herein are novel fusion proteins and nucleic acids encoding these fusion proteins. T cells into which such nucleic acids have been introduced are also contemplated. These T cells can express the fusion proteins on their cell surface. In various embodiments, these T cells can be used in assays to detect costimulatory ligands, inhibitors of costimulatory ligands, or inhibitors that can neutralize an inhibitor of a costimulatory ligand. Such assay methods are also described herein.

35 Claims, 9 Drawing Sheets

FUSION PROTEIN, CELLS EXPRESSING THE FUSION PROTEIN, AND USES THEREOF

This application claims the priority benefit of U.S. Provisional Patent Application No. 62/086,783, filed Dec. 3, 2014, herein incorporated by reference.

This application contains, as a separate part of the disclosure, a Sequence Listing in computer-readable form which is incorporated by reference in its entirety and identified as follows: Filename: 40002_SeqListing.txt; 34,748 bytes, created Nov. 20, 2015.

FIELD

The invention described herein spans the fields of genetic engineering and bioassay development.

BACKGROUND

There is a need in the art for simple, sensitive, and robust bioassays to detect costimulatory activity of various proteins known to costimulate T cells, such as, for example, B7-1 (also known as CD80), B7-2 (also known as CD86), and B7-Related Protein 1 (B7RP1, also known as ICOS Ligand (ICOSL or LICOS), B7 Homolog 2 (B7H2), and GL50) on T cells. Beyond detecting functional costimulatory proteins in samples, such bioassays can be modified to detect therapeutic drugs that inhibit these costimulatory proteins, as well as neutralizing anti-drug antibodies that may develop in dosed subjects and may block the inhibitory activity of such drugs. For example, inhibitors of B7RP1 have potential use as drugs to treat, for example, systemic lupus erythematosus. See, e.g., Kow and Mak (2013), *Costimulatory Pathways: Physiology and Potential Therapeutic Manipulation in Systemic Lupus Erythematosus*, Clinical and Developmental Immunology, Article ID 245928 [online][retrieved Apr. 9, 2014 from Hindawi Publishing Corporation available at http://dx.doi.org/10.1155/2013/245928]. Simple, sensitive, and robust bioassays to detect such therapeutics, as well neutralizing anti-drug antibodies that may develop in patients, are needed.

SUMMARY

Described herein are such bioassays, which utilize novel fusion proteins and cell lines expressing such fusion proteins. These fusion proteins, when expressed on the surface of a T cell, can mediate activation of the T cell in the presence of a costimulatory ligand, without the need for also using an anti-CD3 antibody to initiate signaling through a TCR-CD3 complex. Such fusion proteins comprise at least a portion of the extracellular region of a costimulatory receptor, such as ICOS or CD28, a transmembrane domain, and an intracellular region comprising a tyrosine-based signaling motif and a paired ITAM motif. In addition, nucleic acids, optionally DNAs or RNAs, encoding such fusion proteins are described, as are cells transfected or transduced with these nucleic acids such that they express a fusion protein. Also provided herein are assays that use T cells expressing such fusion proteins to detect a costimulatory ligand, an inhibitor of a costimulatory ligand, or a molecule, e.g., an antibody, that can neutralize an inhibitor of a costimulatory ligand. In the items listed below these aspects of the invention provided herein are described in more detail.

1. A fusion protein comprising the following polypeptides:
   (a) an extracellular region of a costimulatory receptor or a portion thereof;
   (b) a transmembrane domain;
   (c) part or all of the intracellular region of the costimulatory receptor, which comprises at least one tyrosine-based signaling motif; and
   (d) part or all of the intracellular region of a CD3 protein that comprises at least one paired ITAM motif,
   wherein a T cell expressing the fusion protein can be induced to secrete at least three times as much IL-2 by a costimulatory ligand as it secretes in the absence of the costimulatory ligand.

2. The fusion protein of item 1, wherein the T cell expressing the fusion protein can be induced to secrete at least five times as much IL-2 by the costimulatory ligand as it secretes in the absence of the costimulatory ligand.

3. The fusion protein of item 2, wherein the T cell expressing the fusion protein can be induced to secrete at least ten times as much IL-2 by the costimulatory ligand as it secretes in the absence of the costimulatory ligand.

4. The fusion protein of item 3, wherein the T cell expressing the fusion protein can be induced to secrete at least 20 times as much IL-2 by the costimulatory ligand it secretes in the absence of the costimulatory ligand.

5. The fusion protein of item 4, wherein the T cell expressing the fusion protein can be induced to secrete at least 50 times as much IL-2 by the costimulatory ligand as it secretes in the absence of the costimulatory ligand.

6. The fusion protein of item 5, wherein the T cell expressing the fusion protein can be induced to secrete at least 75 times as much IL-2 by the costimulatory ligand as it secretes in the absence of the costimulatory ligand.

7. The fusion protein of item 6, wherein the T cell expressing the fusion protein can be induced to secrete at least 100 times as much IL-2 by the costimulatory ligand as it secretes in the absence of the costimulatory ligand.

8. The fusion protein of any one of items 1 to 7, wherein the tyrosine-based signaling motif has the amino acid sequence of Tyr-Met-Phe-Met (SEQ ID NO:2) or Tyr-Met-Asn-Met (SEQ ID NO:1).

9. The fusion protein of any one of items 1 to 8, wherein the extracellular region or portion thereof of (a) comprises the sequence of amino acids 1-121 of SEQ ID NO:5.

10. The fusion protein of any one of items 1 to 8, wherein the extracellular region or portion thereof of (a) comprises a variant of the sequence of amino acids 1-121 of SEQ ID NO:5 that is at least 90% identical to the sequence amino acids 1-121 of SEQ ID NO:5.

11. The fusion protein of item 10, wherein the extracellular region or portion thereof of (a) comprises a variant of the sequence of amino acids 1-121 of SEQ ID NO:5 that is at least 95% identical to the sequence amino acids 1-121 of SEQ ID NO:5.

12. The fusion protein of item 11, wherein the extracellular region or portion thereof of (a) comprises a variant of the sequence of amino acids 1-121 of SEQ ID NO:5 that is at least 98% identical to the sequence amino acids 1-121 of SEQ ID NO:5.

13. The fusion protein of any one of items 1 to 8, wherein the extracellular region or portion thereof of (a) comprises the amino acid sequence of amino acids 1-135 of SEQ ID NO:6.

14. The fusion protein of any one of items 1 to 8, wherein the extracellular region or portion thereof of (a) comprises a variant of the sequence of amino acids 1-135 of SEQ ID NO:6 that is at least 90% identical to the sequence amino acids 1-135 of SEQ ID NO:6.

15. The fusion protein of item 14, wherein the extracellular region or portion thereof of (a) comprises a variant of the sequence of amino acids 1-135 of SEQ ID NO:6 that is at least 95% identical to the sequence amino acids 1-135 of SEQ ID NO:6.

16. The fusion protein of item 15, wherein the extracellular region or portion thereof of (a) comprises a variant of the sequence of amino acids 1-135 of SEQ ID NO:6 that is at least 98% identical to the sequence amino acids 1-135 of SEQ ID NO:6.

17. The fusion protein of any one of items 1 to 12, wherein the costimulatory ligand comprises the amino acid sequence of amino acids 1-117 of SEQ ID NO:3.

18. The fusion protein of item 17, wherein the costimulatory ligand comprises the amino acid sequence of amino acids 1-234 of SEQ ID NO:3.

19. The fusion protein of any one of items 1 to 8 and 13-16, wherein the costimulatory ligand comprises the amino acid sequence of amino acids 1-220 of SEQ ID NO:4.

20. The fusion protein of any one of items 1 to 8 and 13-16, wherein the costimulatory ligand comprises the amino acid sequence of amino acids 1-208 of SEQ ID NO:7.

21. The fusion protein of any one of items 1 to 20, wherein the intracellular region of (c) comprises the amino acid sequence of Tyr-Met-Phe-Met (SEQ ID NO:2).

22. The fusion protein of item 21, wherein the intracellular region of (c) comprises the amino acid sequence at least 90% identical to amino acids 145-179 of SEQ ID NO:5.

23. The fusion protein of item 22, wherein the intracellular region of (c) comprises an amino acid sequence at least 95% identical to the sequence of amino acids 145-179 of SEQ ID NO:5.

24. The fusion protein of item 23, wherein the intracellular region of (c) comprises an amino acid sequence at least 98% identical to the sequence of amino acids 145-179 of SEQ ID NO:5.

25. The fusion protein of item 24 comprising the amino acid sequence of amino acids 145-179 of SEQ ID NO:5.

26. The fusion protein of any one of items 1 to 20, wherein the intracellular region of (c) comprises the amino acid sequence of Tyr-Met-Asn-Met (SEQ ID NO:1).

27. The fusion protein of item 26, wherein the intracellular region of (c) comprises an amino acid sequence at least 90% identical to the sequence of amino acids amino acids 159-202 of SEQ ID NO:6.

28. The fusion protein of item 27, wherein the intracellular region of (c) comprises an amino acid sequence at least 95% identical to the sequence of amino acids amino acids 159-202 of SEQ ID NO:6.

29. The fusion protein of item 28, wherein the intracellular region of (c) comprises an amino acid sequence at least 98% identical to the sequence of amino acids amino acids 159-202 of SEQ ID NO:6.

30. The fusion protein of item 29, wherein the intracellular region of (c) comprises the amino acid sequence of amino acids 159-202 of SEQ ID NO:6.

31. The fusion protein of any one of items 1 to 30, wherein the transmembrane domain of (b) comprises an amino acid sequence at least 90% identical to amino acids 122-144 of SEQ ID NO:5.

32. The fusion protein of item 31, wherein the transmembrane domain of (b) comprises an amino acid sequence at least 95% identical to amino acids 122-144 of SEQ ID NO:5.

33. The fusion protein of item 32, wherein the transmembrane domain of (b) comprises an amino acid sequence at least 98% identical to amino acids 122-144 of SEQ ID NO:5.

34. The fusion protein of item 33, wherein the transmembrane domain of (b) comprises the amino acid sequence of amino acids 122-144 of SEQ ID NO:5.

35. The fusion protein of any one of items 1 to 30, wherein the transmembrane domain of (b) comprises an amino acid sequence at least 90% identical to amino acids 136-158 of SEQ ID NO:6.

36. The fusion protein of item 35, wherein the transmembrane domain of (b) comprises an amino acid sequence at least 95% identical to amino acids 136-158 of SEQ ID NO:6.

37. The fusion protein of item 36, wherein the transmembrane domain of (b) comprises an amino acid sequence at least 98% identical to amino acids 136-158 of SEQ ID NO:6.

38. The fusion protein of item 37, wherein the transmembrane domain of (b) comprises the sequence of amino acids 136-158 of SEQ ID NO:6.

39. The fusion protein of any one of items 1 to 38, wherein the part or all of the intracellular region of the CD3 protein comprises the sequence of amino acids 138-152 of SEQ ID NO:10.

40. The fusion protein of item 39, wherein the CD3 protein is human CD3γ.

41. The fusion protein of item 40, wherein the part or all of the intracellular region of the CD3 protein comprises the sequence of amino acids 138-160 of SEQ ID NO:10.

42. The fusion protein of any one of items 1 to 38, wherein the part or all of the intracellular region of the CD3 protein comprises the sequence of amino acids 166-180 of SEQ ID NO:9.

43. The fusion protein of item 42, wherein the CD3 protein is human CD3ε.

44. The fusion protein of item 43, wherein the part or all of the intracellular region of the CD3 protein comprises the sequence of amino acids 166-185 of SEQ ID NO:9.

45. The fusion protein of any one of items 1 to 38, wherein the part or all of the intracellular region of the CD3 protein comprises the sequence of amino acids 128-142 of SEQ ID NO:11.

46. The fusion protein of item 45, wherein the CD3 protein is human CD3δ.

47. The fusion protein of item 46, wherein the part or all of the intracellular region of the CD3 protein comprises the sequence of amino acids 128-150 of SEQ ID NO:11.

48. The fusion protein of any one of items 1 to 38, wherein the part or all of the intracellular region of the CD3 protein comprises the sequence of amino acids 51-65 of SEQ ID NO:8.

49. The fusion protein of any one of items 1 to 38 and 48, wherein the part or all of the intracellular region of the CD3 protein comprises the sequence of amino acids 90-105 of SEQ ID NO:8.

50. The fusion protein of any one of items 1 to 38, 48, and 49, wherein the part or all of the intracellular region of the CD3 protein comprises the sequence of amino acids 121-135 of SEQ ID NO:8.

51. The fusion protein of any one of items 1 to 38 and 48 to 50, wherein the CD3 protein is human CD3ζ.

52. The fusion protein of item 51, wherein the part or all of the intracellular region of the CD3 protein comprises the sequence of amino acids 51-135of SEQ ID NO:8.

53. The fusion protein of item 52, wherein the part or all of the intracellular region of the CD3 protein comprises the sequence of amino acids 40-143 of SEQ ID NO:8.

54. A fusion protein comprising the amino acid sequence of SEQ ID NO:12.

55. A fusion protein comprising the amino acid sequence of SEQ ID NO:14.

56. A nucleic acid encoding a fusion protein of any one of items 1 to 55.

57. A T cell containing the nucleic acid of item 56.

58. The T cell of item 57, which expresses the fusion protein of any one of items 1 to 55.

59. The T cell of item 58, which is a primary T cell.

60. The T cell of item 58, which is an immortalized T cell.

61. The T cell of item 60, which is from a T cell lymphoma cell line or a T cell leukemia cell line.

62. A method for determining the concentration of a bioactive costimulatory ligand in a test sample comprising:
(a) providing T cells that express the fusion protein of any one of items 1 to 55;
(b) determining the level of a signal indicating T cell activation in the following kinds of samples: (1) in the absence of both the test sample and the costimulatory ligand, (2) in the presence of varying concentrations of the test sample, and (3) in the presence of varying known concentrations of the costimulatory ligand; and
(c) comparing the signals detected in the presence of varying concentrations of the test sample with those detected in the presence of varying levels of costimulatory ligand, thereby determining the concentration of the bioactive costimulatory ligand in the test sample.

63. The method of item 62, wherein the signal determined in (b) is from an assay for IL-2 secreted by the T cells.

64. A method for determining the concentration of a bioactive inhibitor of a costimulatory ligand in a test sample comprising:
(a) providing T cells that express the fusion protein of any one of items 1 to 55;
(b) determining the level of a signal indicating T cell activation in the following kinds of samples: (1) in the absence of the test sample and in the presence of a constant amount of the costimulatory ligand sufficient such that the signal produced by the T cells is at least twice as large as it is in the absence of the costimulatory ligand, (2) in the presence of the constant amount of the costimulatory ligand and varying concentrations of the test sample, and (3) in the presence of the constant amount of the costimulatory ligand and varying known concentrations of the inhibitor; and
(c) comparing the signals determined in (b)(2) with those detected in (b)(3) to determine the concentration bioactive inhibitor in the test sample.

65. The method of item 64, wherein the amount of the costimulatory ligand in step (b) is sufficient to induce the T cells to produce a signal at least four times as large as they produce in the absence of the costimulatory ligand.

66. The method of item 64 or 65, wherein the one or more signals are from an assay for IL-2 secreted by the T cells.

67. A method for determining the presence of antibodies that neutralize an inhibitor of a costimulatory ligand in a test sample comprising:
(a) providing T cells that expresses the fusion protein of any one of items 1 to 55;
(b) determining the level of a signal indicating T cell activation in the following kinds of samples: (1) in the presence of constant concentrations of both the costimulatory ligand and the inhibitor, wherein the constant concentration of the costimulatory ligand is sufficient, in the absence of the inhibitor, to induce the T cells to produce a signal at least five times as large as they produce in the absence of the costimulatory ligand, wherein the constant concentration of the inhibitor is sufficient, in the presence of the constant concentration of the costimulatory ligand, to provide at least a three-fold reduction in the signal; (2) in the presence of the constant concentrations of both the costimulatory ligand and the inhibitor of the costimulatory ligand and in the presence of a known concentration of one or more antibodies that neutralize the inhibitor; and (3) in the presence of the constant concentrations of both the costimulatory ligand and the inhibitor of the costimulatory ligand and in the presence of a test sample; and
(c) comparing the signals obtained in (b)(2) and (b)(3), each normalized to the value obtained in (b)(1), to determine the presence of antibodies in the test sample that neutralize the inhibitor.

68. The method of item 68, wherein the one or more signals are from an assay for IL-2 secreted by the T cells.

BRIEF DESCRIPTION OF THE FIGURES

In FIG. 2A, the paired ovals outlined with dotted lines represent dimeric B7RP1 that is added to the assay as part of a sample. In FIG. 2B, dimeric B7RP1 is part of the assay mixture (represented by paired ovals outlined with solid lines), and a B7RP1 inhibitor (inverted V shape with dotted lines) is added as part of a sample being assayed. In FIG. 2C, dimeric B7RP1 (represented by paired ovals outlined with solid lines) and the B7RP1 inhibitor (inverted V shape with solid lines) are part of the assay mixture, and neutralizing antibodies that bind to the B7RP1 inhibitor (Y shape with dotted lines) are added as part of the test sample being assayed.

FIG. 4A, FIG. 4B, and FIG. 4C diagram three different fusion protein constructs that contain varying amounts of the intracellular region of CD3ζ, which are called, respectively ICOS-CD3 I, ICOS-CD3 II, and ICOS-CD3 III, respectively. As indicated in all panels, the left-most open rectangle labeled "ICOS" represents the extracellular region of human ICOS, which contains the sequence of amino acids 1-121 of SEQ ID NO:5. The open rectangle labeled "TM" represents the transmembrane regions of human ICOS, which contains the sequence of amino acids 122-144 of SEQ ID NO:5. The following open rectangle labeled "ICOS" represents the intracellular region of human ICOS, which contains amino acids 145-179 of SEQ ID NO:5. In FIG. 4A and FIG. 4B, the filled rectangles represent portions of the intracellular region of CD3ζ that are proximal to its transmembrane domain, which contain the sequence of amino acids 31-39 and 35-39 of SEQ ID NO:8, respectively. In FIG. 4A-C, the open rectangle labeled CD3ζ represents amino acids 40-143 of SEQ ID NO:8. Thus, the construct of FIG. 4A contains the entire intracellular region of CD3ζ plus two amino acids of the transmembrane portion of CD3ζ, whereas the constructs of FIG. 4B and FIG. 4C are missing different portions of the intracellular region of CD3ζ immediately downstream from the transmembrane domain of CD3ζ.

BRIEF DESCRIPTION OF THE SEQUENCES

Figure 1:
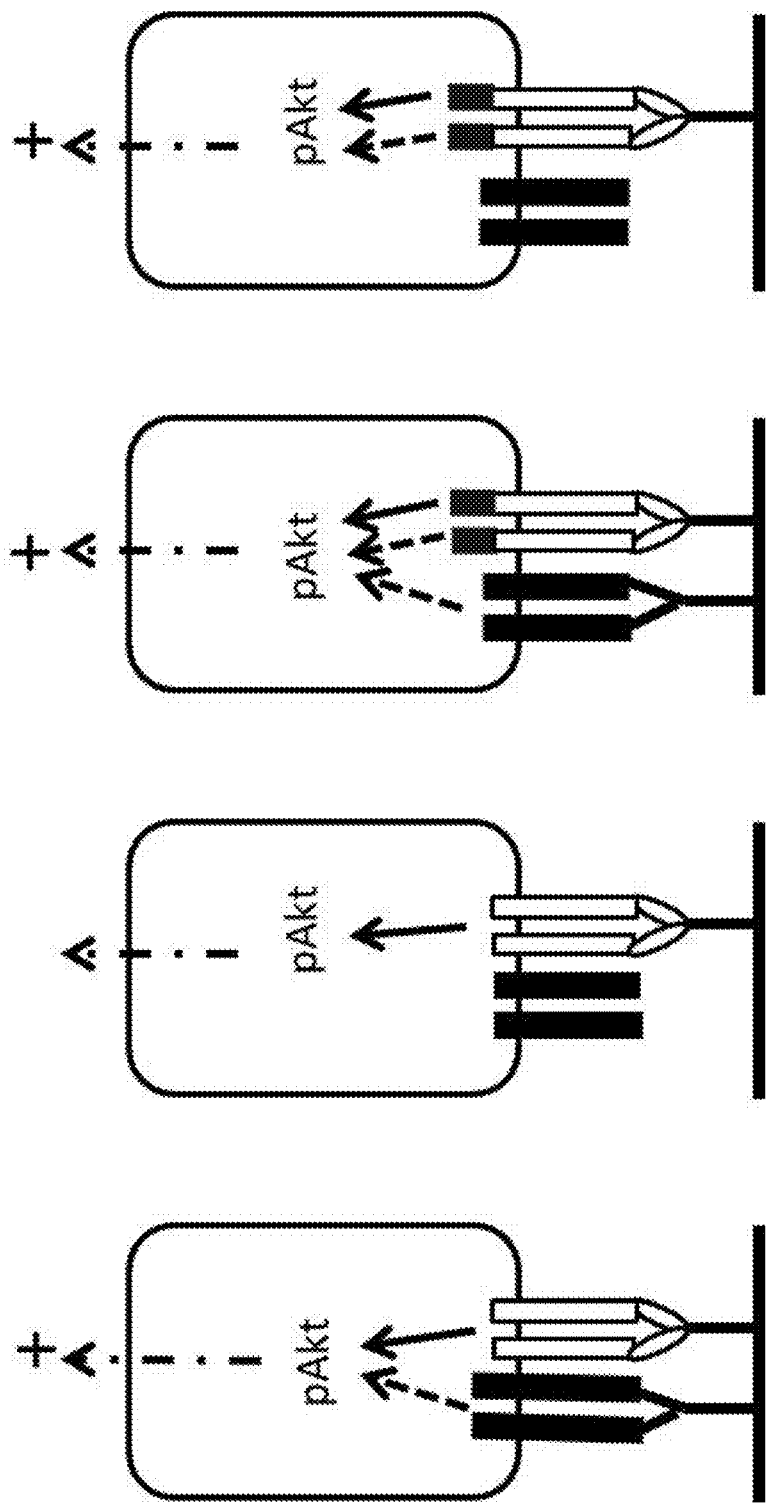
FIG. 1: Activation of T cells expressing ICOS or an ICOS-CD3fusion protein. The large rectangles with rounded corners represent T cells expressing the components of the PI3 kinase-Akt pathway. The small vertical, solidly-filled rectangles represent a T cell receptor (TCR)-CD3 complex and the vertical, unfilled rectangles represent ICOS. The vertical rectangles that are partially unfilled and partially filled represent fusion proteins, such as the ICOS-CD3 proteins described herein or variants thereof described herein. The solid Y-shaped figure represents an anti-CD3 antibody, which can elicit signaling via the TCR-CD3 complex. The Y-shaped figure in which the arms of the Y are two unfilled ovals represents a dimeric B7RP1-Fc molecule, which can elicit a costimulatory signal via ICOS. The solid and dashed arrows within the cell represent, respectively, activation signals coming from ICOS and the TCR-CD3 complex when they are engaged by B7RP1-Fc or the anti-CD3 antibody, respectively. The upward-pointing dash-dot arrow spanning the perimeter of the cell represents an indication of activation (+) or lack thereof (−) coming from cell. Note that engagement of ICOS by B7RP1-Fc alone, i.e., in the absence of anti-CD3 antibodies, is not sufficient to trigger the PI3 kinase-Akt (pAkt) signaling pathway. Secretion of IL-2 or IL-8 can indicate T cell activation and lack of secretion of these cytokines can indicate lack of activation. Alternatively, other indices of activation can be measured, for example the phosphorylation status of Akt or T cell proliferation, as explained in detail below. Note that anti-CD3 antibodies and the B7RP1-Fc protein need to be coated onto a solid support (i.e., plate surface or microbeads) in order to efficiently crosslink their respective receptors. Anti-CD3 antibodies are passively coated onto the plate, while B7RP1-Fc protein is actively captured by plate-bound anti-Fc or non-neutralizing anti-B7RP1 antibodies.

| SEQ ID NO | Description |
| --- | --- |
| 1 | Amino acid sequence of tyrosine-based motif |
| 2 | Amino acid sequence of tyrosine-based motif |
| 3 | Amino acid sequence of mature human B7RP1 |
| 4 | Amino acid sequence of mature human B7-2 |
| 5 | Amino acid sequence of mature human ICOS |

-continued

| SEQ ID NO | Description |
|---|---|
| 6 | Amino acid sequence of mature human CD28 |
| 7 | Amino acid sequence of mature human B7-1 |
| 8 | Amino acid sequence of mature human CD3ζ |
| 9 | Amino acid sequence of mature human CD3ε |
| 10 | Amino acid sequence of mature human CD3γ |
| 11 | Amino acid sequence of mature human CD3δ |
| 12 | Amino acid sequence of a mature ICOS-CD3 fusion protein (ICOS-CD3 III) |
| 13 | Nucleic acid sequence encoding the amino acid sequence of SEQ ID NO:12 |
| 14 | Amino acid sequence of a mature ICOS-CD3 fusion protein (ICOS-CD3 II) |
| 15 | Nucleic acid sequence encoding the amino acid sequence of SEQ ID NO:14 |
| 16 | Amino acid sequence of a mature ICOS-CD3 fusion protein (ICOS-CD3 I) |
| 17 | Nucleic acid sequence encoding the amino acid sequence of SEQ ID NO:16 |
| 18 | Amino acid sequence of mature murine ICOS |
| 19 | Amino acid sequence of mature murine CD28 |

DETAILED DESCRIPTION

Activation of T cells requires engagement of a T cell receptor-CD3 (TCR-CD3) complex, as well as costimulation via a costimulatory cell surface receptor, such as Inducible Co-Stimulator (ICOS) or CD28. For example, signaling in a T cell via ICOS is generally detected by measuring a parameter indicative of T cell activation, for example cytokine secretion or T cell proliferation, but assays to detect such signaling have been difficult to develop and were unsatisfactory for a number of reasons. First, primary naïve T cells and most T cell lines do not constitutively express ICOS, and, therefore, ICOS expression must be achieved by other means, such as induction or transfection, if ICOS signaling is to be effectively assayed. Additionally, ICOS signaling is difficult to trigger because it requires simultaneous engagement of ICOS with the ICOS ligand B7RP1 and of the TCR-CD3 complex with an anti-TCR-CD3 complex antibody (typically an anti-CD3 antibody). Moreover, existing assays of B7RP1-induced ICOS signaling have limited sensitivity and assay response range, likely due to the insufficient signaling capabilities and/or low expression levels of ICOS.

To address these issues, described herein are T cell lines that express high levels of a chimeric cell surface protein including part or all of a costimulatory receptor, such as ICOS or CD28, or a variant thereof, including at least parts of the extracellular region of the costimulatory receptor or the variant, a transmembrane domain, an intracellular region comprising a tyrosine-based signaling motif, and another intracellular region comprising at least one paired ITAM motif, which, optionally, can be part of an intracellular region of a CD3 chain. The intracellular region comprising the tyrosine-based signaling motif can include part or all of the intracellular region of the costimulatory receptor. This approach integrates the signaling events from a costimulatory receptor, such as ICOS or CD28, and the TCR-CD3 complex and provides robust expression of the chimeric cell surface protein. Hence, activation of the genetically-engineered T cells can be triggered by engagement of the chimeric cell surface protein with a costimulatory ligand, such as the ICOS ligand B7RP1 (or, in alternative embodiments with B7-1 or B7-2), without the need for engagement of the TCR-CD3 complex or induction of ICOS expression. The use of these genetically engineered T cells provides a simplified assay for ICOS or CD28 signaling and also substantially increases the sensitivity and assay response range compared to existing assays.

Definitions

A "B7RP1 inhibitor," as meant herein, can reduce the activity of a protein comprising the extracellular region of human B7RP1, i.e., residues 1-235 of SEQ ID NO:3, in an assay performed as described in Example 5, where the B7RP1 inhibitor is added to an assay mixture comprising a (1) T cell expressing ICOS-CD3ζ fusion protein comprising the amino acid sequence of SEQ ID NO:12 and (2) a protein comprising the extracellular region of human B7RP1. Similarly, an "inhibitor" of a different costimulatory ligand, for example an inhibitor of B7-1 or B7-2, can reduce the activity of a protein comprising the extracellular region of B7-1 or B7-2 in a similar assay.

A "bioactive" substance, which can be a polypeptide, is one that exhibits activity in a biological assay, which can be an in vitro or in vivo assay.

A "test sample," as meant herein, can be any liquid subjected to an assay using the methods described herein to determine the presence and/or the levels of a (1) costimulatory ligand, (2) an inhibitor of a costimulatory ligand, or costimulatory receptor, which can be a therapeutic, and/or (3) an antagonist of the inhibitor of (2), which can be, for example, an anti-drug antibody.

A "costimulatory receptor," as meant herein, is a receptor that can, when engaged by its "costimulatory ligand," or an artificial substitute for such ligand, mediate a signal in a "T cell," which, when combined with a signal from a "T cell receptor-CD3" (TCR-CD3) complex engaged by its ligand, or a substitute for such a ligand, result in the activation or enhancement of activation of the T cell. Hence, this definition excludes the so-called negative or inhibitory costimulatory receptors, such as CTLA-4 or PD-1. A common substitute ligand that can be used to stimulate a TCR-CD3 complex is an anti-CD3 antibody. A substitute ligand that can be used to stimulate ICOS, a costimulatory receptor, is an anti-ICOS antibody. A "costimulatory receptor," is selected from the group of receptors comprising a single extracellular immunoglobulin-variable region-like domain, plus an extracellular stalk, followed by a transmembrane domain and an intracellular region comprising one or more tyrosine-based signaling motifs. See, e.g., Chattopadhyay et al. (2009), Immunol. Rev. 229(1): 356-386, the portions of which describe this group of receptors are incorporated herein by reference. This group includes Inducible T Cell Costimulator (ICOS, also known as Activation-Inducible Lymphocyte Immunomediatory Molecule (AILIM)) and CD28, which, as meant herein, can be from any mammalian or avian species or can be variants of any of these proteins that comprise an amino acid sequence at least 90%, 95%, or 98% identical to the naturally-occurring amino acid sequence and that retain their costimulatory activity. For example, a variant can comprise an amino acid sequence at least 90%, 95%, or 98% identical to any one of SEQ ID NOs:5, 6, 12, 14, 18, and/or 19 and can mediate similar costimulatory activity when expressed on the surface of a T cell to that mediated by the unaltered protein. As is known in the art, CD28 and ICOS mediate costimulatory signals in T cells.

The intracellular region of a costimulatory receptor contains at least one "tyrosine-based signaling motif." A tyrosine-based signaling motif is an amino acid sequence 2-16 amino acids in length that includes at least one tyrosine. Specifically included within "tyrosine-based signaling motifs" are the following amino acid sequences: Tyr-Met- Asn-Met (SEQ ID NO: 1); Tyr-Met-Phe-Met (SEQ ID NO: 2); Tyr-Val-Lys-Met (SEQ ID NO: 20); and Thr-Glu-Tyr-Ala-Thr-Ile (SEQ ID NO: 21).

A "costimulatory ligand," as meant herein, is a protein that can elicit costimulatory activity, i.e., T cell activation, when it engages with a "costimulatory receptor" expressed on the surface of a T cell, as described below. In addition, a costimulatory ligand can be confined to proteins comprising amino acid sequences that are the same or similar to the amino acid sequences of the extracellular regions of B7RP1, B7-1, and B7-2, which may be of mammalian or avian origin. Encompassed within costimulatory ligands are variants of any of these proteins that comprise sequences at least 90%, 95%, or 98% identical to the sequences of the extracellular regions of these proteins and that can elicit costimulatory activity similar to that detected with a polypeptide comprising the unaltered extracellular region. More particularly, included within costimulatory ligands are proteins comprising the amino acid sequence of amino acids 1-235 of SEQ ID NO:3, amino acids 1-208 of SEQ ID NO:7, or amino acids 1-220 of SEQ ID NO:4 and proteins that are at least 90%, 95%, or 98% identical to any of these sequences.

"Substitutes for costimulatory ligands," as meant herein, are proteins other than a "costimulatory ligand" that can engage a "costimulatory receptor" expressed on the surface of a T cell to elicit T cell activation. Such substitutes for costimulatory ligands include, for example, antibodies that that can bind to a costimulatory receptor and thereby initiate signaling by the receptor. Examples of such antibodies include anti-ICOS antibodies and anti-CD28 antibodies.

An "inhibitor of a costimulatory ligand," as meant herein, is a molecule that can inhibit the activation of a T cell by a costimulatory ligand, for example, in an assay like that described in Example 5. In some embodiments, such inhibitors can be antibodies that bind to the costimulatory ligand or its costimulatory receptor.

A "T cell," as meant herein, is a kind of lymphocyte that has many subtypes, most of which mature in the thymus and are, hence, referred to as T cells. There are various kinds of T cells, such as helper T cells, cytotoxic T cells, memory T cells, regulatory T cells, natural killer T cells, mucosal associated invariant T cells, and gamma delta T cells (γδ T cells). These different kinds of T cells express different proteins on their cell surfaces, and these cell surface markers can serve to identify different subclasses of T cells. Generally, all subtypes of T cells can be identified by their expression of a TCR-CD3 complex. As meant herein, T cells can also be immortalized cell lines derived from any of the above mentioned T lymphocyte subsets. There are at least three kinds of TCRs. An αβPTCR complex contains a heterodimer consisting of TCRα and TCRβ (αβTCR), a homodimer consisting of two CD3ζproteins (CD3ζζ), a heterodimer consisting of CD3δ and CD3ε (CD3δε), and a heterodimer consisting of CD3γ and CD3ε (CD3γε). A γδTCR complex contains a heterodimer consisting of TCRγ and TCRδ (γδTCR), plus CD3δε and CD3γε heterodimers and a CD3ζζ homodimer. A pTCR consists of a heterodimer consisting of pTα and TCRβ, plus CD3δε and CD3γε heterodimers and a CD3ζζ homodimer. See, e.g., Kuhns and Badgandi (2012), Immunological Rev. 250: 120-143, the relevant portions of which are incorporated by reference herein. As meant herein, T cells can be identified and isolated by fluorescence-activated cell sorting (FACS) using a fluorescently labeled anti-CD3 antibody and/or a fluorescently labeled anti-TCR antibody. T cells can also be isolated from a complex mixture of cells using, for example, a T cell isolation kit such as the Pan T Cell Isolation Kit, human from Miltenyi Biotec (order no. 130-096-535).

"T cell activation," as meant herein, can be detected in a variety of ways. Possible ways to detect T cell activation are increases in IL-2, IL-4, IL-5, IL-6, IL-10, IFNγ, TNFα, or IL-21 secretion, phosphorylation of ITAMs in intracellular regions of surface receptors, phosphorylation of intracellular signaling molecules (for example phospho-Akt), increased calcium flux, upregulation of CD69, and increased T cell proliferation. See, e.g., Yong, Salzer, Grimbacher (2009), Immunol. Reviews 229: 101-113; Lindsey et al. (2007), Cytotherapy 9(2):123-32., Rabinowitz et al. (1996), Immunity 5(2): 125-135. The portions of these references that describe such methods are incorporated herein by reference. Commercial kits for detecting IL-2, IL-4, IL-5, IL-6, IL-10, IFNγ, TNFα, or IL-21 are available, for example, from Meso Scale Discovery (MSD, www.mesoscale.com). The Human IL-2 Tissue Culture Kit (Meso Scale Discovery Catalog No. K151AHB-1), the V-Plex Human Cytokine 30-plex Kit (Meso Scale Discovery Catalog No. K15054D-1), and the Human IL-21 Platinum ELISA kit (Affimetrix, BMS2043) can be used to detect these cytokines. Proliferation can be detected by flow cytometry using DAPI/PI staining and/or by using a CellTiter-Glo® Luminescent Cell Viability Assay (Promega, G7570). In addition, ITAMs in intracellular regions of TCR-CD3 complex proteins are phosphorylated when T cells are activated, as are other intracellular signaling molecules (for example phospho-Akt). Such phosphorylatation can be detected by flow cytometry, immunoassays, or Western blots using phospho-specific antibodies and fluorescently-labelled or otherwise-labelled detection antibodies. Further, CD69, a cell surface glycoprotein, is upregulated on activated T cells, which can be detected by flow cytometry using an anti-CD69 antibody plus an appropriate fluorescently-labeled secondary antibody for detection. Calcium flux is also increased in activated T cells, which can be detected by fluorescent dyes, such as Indo-1, that change their wavelength of light emission when intracellular calcium concentrations change. (Yong, Salzer, Grimbacher Immunol. Reviews 2009; Vol 229:101-113; Lindsey et al. Cytotherapy. 2007;9(2):123-32., Rabinowitz et al. Immunity, Volume 5, Issue 2, p125-135, 1 Aug. 1996).

A "CD3 protein," as meant herein, is a CD3γ, CD3δ, CD3ε, or CD3ζ chain from a mammalian or avian species, e.g., human, primate, mouse, rat, rabbit, hamster, or chicken etc.

An "extracellular region," as meant herein, is the portion of a membrane-spanning protein that is displayed on the outside of a cell when the protein is expressed on the cell surface. On a practical level, an extracellular region can be located by analyzing an amino acid sequence using software that will identify the transmembrane domain(s) of a protein and the portion(s) that are outside and inside the cell, such as TMHMM (see, e.g., Krogh et al. (2001), J. Mol. Biol. 305: 567-580, which is incorporated by reference herein). For prediction of the location of the signal sequence, SignalP V2.0.b2-HMM can be used (see Kerstin et al. (2000), Bioinformatics Applications Note 16(8): 741-742, the relevant portions of which are incorporated herein by reference).

A "fusion protein," as meant herein, is a protein in which amino acid sequences found in two different proteins are fused together. For example, fusion of an amino acid sequence of an Fc region of an antibody with part or all of an amino acid sequence of B7RP1 creates a fusion protein.

Similarly, fusion of part or all of the amino acid sequence of ICOS with part or all of the amino acid sequence of CD3ζ also creates a fusion protein.

A "human" nucleic acid or protein is one that has a nucleotide or amino acid sequence that is the same or very similar to a sequence that naturally occurs in a human. Similarly, a "human" nucleotide or amino acid sequence is sequence that is the same or "very similar" to a sequence that naturally occurs in a human. A very similar amino acid sequence has no more than 5 or 10 substitutions, insertions, and/or deletions of a single amino acid per 100 amino acids of sequence relative to a naturally-occurring human amino acid sequence, and a protein containing such a sequence also retains the biological activity of the naturally occurring human protein. Further, a very similar nucleotide sequence, as meant herein, encodes an amino acid sequence that is very similar to a naturally occurring human amino acid sequence. In the context of the fusion proteins described herein, which can contain "human" proteins or portions thereof, the relevant biological activity is the ability of a T cell having a fusion protein expressed on its surface to become activated by a costimulatory ligand as measured by secretion of at least three times as much IL-2 in the presence of an appropriate amount of a costimulatory ligand as is secreted in the absence of the costimulatory ligand.

An "intracellular region," as meant herein, is the portion of a membrane-spanning protein that is located inside the cell when the protein is expressed by the cell. On a practical level, an intracellular region can be located by analyzing an amino acid sequence using software that will identify the transmembrane domain(s) of a protein and the portion(s) that are outside and inside the cell, such as TMHMM (see, e.g., Krogh et al. (2001), J. Mol. Biol. 305: 567-580, which is incorporated by reference herein). For prediction of the location of the signal sequence, SignalP V2.0.b2-HMM can be used (see Kerstin et al. (2000), Bioinformatics Applications Note 16(8): 741-742, the relevant portions of which are incorporated herein by reference).

A "paired ITAM motif," as meant herein, is an amino acid sequence consisting of YXXL/I-$X_{6-8}$-YXXL/I, where "Y" represent tyrosine, "L/I" means that leucine or isoleucine can be at this position, and X represents any amino acid.

A "mature" protein, as meant herein, is one lacking its signal sequence, whereas a precursor of the mature protein contains the signal sequence. The signal sequence is typically located at the amino terminus of a protein and is cleaved during the process of maturation and secretion of a protein. On a practical level, a signal sequence can be located by analyzing an amino acid sequence using software that will identify the signal sequence, such as SignalP V2.0.b2. See, e.g., Kerstin et al. (2000), Bioinformatics Applications Note 16(8): 741-742, which is incorporated herein by reference.

The activity of a protein is considered to be "neutralized" by a molecule, such as an anti-drug antibody, if the activity of the protein in the presence of the molecule in an assay is not detectable or is substantially reduced as compared to the activity detected in the absence of the molecule. Activity is considered to be substantially reduced if it is 80% or less, 70% or less, 50% or less, 25% or less, 10% or less, or 5% or less as compared to activity detected in the absence of the molecule. In embodiments were the protein being neutralized is, itself, an inhibitor of the activity being measured, the molecule is said to "neutralize" the protein if the amount of inhibition of the activity by the protein is 80% or less, 70% or less, 50% or less, 25% or less, 10% or less, or 5% or less of what it would be in the absence of the molecule.

As meant herein, "percent identity," of two amino acid or nucleic acid sequences can be determined using the computer programs of the Genetics Computer Group (GCG; Madison, Wis.) Wisconsin package version 10.0 program, GAP (Devereux et al. (1984), Nucleic Acids Res. 12: 387-95). The preferred default parameters for the GAP program includes: (1) The GCG implementation of a unary comparison matrix (containing a value of 1 for identities and 0 for non-identities) for nucleotides, and the weighted amino acid comparison matrix of Gribskov and Burgess, ((1986) Nucleic Acids Res. 14: 6745) as described in *Atlas of Polypeptide Sequence and Structure*, Schwartz and Dayhoff, eds., National Biomedical Research Foundation, pp. 353-358 (1979) or other comparable comparison matrices; (2) a penalty of 8 for each gap and an additional penalty of 2 for each symbol in each gap for amino acid sequences, or a penalty of 50 for each gap and an additional penalty of 3 for each symbol in each gap for nucleotide sequences; (3) no penalty for end gaps; and (4) no maximum penalty for long gaps. Although these programs can report a high percent identity for an alignment that spans only a portion of the sequences entered, as meant herein, a given sequence has a stated percent identity with another sequence only if at least 80%, 90%, 95%, 97%, or 100% of the length of at least one of the sequences is aligned to the other by GAP. For example, if two sequences, one of 100 amino acids and the other of 120 amino acids, were aligned, and GAP reported a percent identity of 90%, the sequences would only be considered 90% identical if the alignment presented by GAP spanned at least 80 amino acids, in which there could be mismatches or gaps. Thus, the alignment need not be perfectly matched for 80 amino acids, but the sequences must be compared over a span of 80 amino acids. If, for example, the alignment spanned only 60 amino acids, it would not be considered 90% identical as meant herein.

A "polypeptide," as meant herein, is a molecule made up of amino acids joined by peptide bonds. Generally, a polypeptide will be at least 10 amino acids long and can be part of a larger polypeptide or protein. The protein may be multimeric. Generally, a polypeptide is a single chain of amino acids.

A "protein," as meant herein, can comprise a single polypeptide or multiple polypeptides fused together in a single polypeptide chain, i.e., a "fusion protein." In some embodiments, a protein can be multimeric, i.e., can contain multiple polypeptide chains.

A "transmembrane domain," as meant herein, is a hydrophobic portion of a protein that localizes to the cell membrane when the protein is expressed in a cell. Herein, transmembrane domains have been identified using TMHMM (see, e.g., Krogh et al. (2001), J. Mol. Biol. 305: 567-580, which is incorporated by reference herein), and a stretch of amino acids predicted by TMHMM to localize to a cell membrane is a "transmembrane domain," as meant herein.

Assays

Full activation of a T cell ordinarily requires a primary signal mediated through a TCR-CD3 complex along with a costimulatory signal mediated through an interaction between a costimulatory receptor and ligand. See, e.g., Wilson et al. (2006), J. Immunol. 177(4): 2365-2372. The activation of a T cell is mediated by intracellular signaling pathways including phosphoinositide-3 kinase (PI3K) and protein kinase B (PKB, also called Akt) activation. See, e.g., Song et al. (2008), Cell. & Mol. Biol. 5(4): 239-247. The CD3 chains of a TCR-CD3 complex mediate an intracellular signal upon engagement of the TCR with an antigen displayed by an MHC molecule. In vitro assays often utilize an anti-CD3 antibody to mimic this signal. The costimulatory signal can be derived from engagement of a variety of costimulatory receptors expressed on T cells, e.g. CD28 or ICOS, with their ligands. Id. Stimulation of a T cell expressing ICOS with B7RP1 plus an anti-CD3 antibody can activate a T cell or increase its state of activation, whereas stimulation with B7RP1 alone does not result in increased T cell activation. Activation of T cells can be detected in a number of ways. For example, activated T cells proliferate and secrete cytokines, including IL-2, IL-4, IL-5, IL-6, IL-10, IFNγ, TNFα, and IL-21. These cytokines can be detected using commercially available kits such as the Human IL-2 Tissue Culture kit (Meso Scale Discovery, K151AHB-1), the V-PLEX Human Cytokine 30-plex kit (Meso Scale Discovery, K15054D-1) and the Human IL-21 Platinum ELISA kit (Affimetrix, BMS2043). Detection of IL-2 is described in Example 2 below. Proliferation can be detected by flow cytometry using DAPI/PI staining, or by using a CellTiter-Glo® Luminescent Cell Viability Assay (Promega, G7570). In addition, ITAMs in intracellular regions of TCR-CD3 complex proteins are phosphorylated, as are other intracellular signaling molecules (for example phospho-Akt). Such phosphorylatation can be detected using phospho-specific antibodies. Further, CD69, a cell surface glycoprotein, is upregulated on activated T cells, which can be detected by flow cytometry using an anti-CD69 antibody plus an appropriate fluorescently-labeled secondary antibody for detection. Calcium flux is also increased in activated T cells, which can be detected by fluorescent dyes, such as Indo-1, that change their wavelength of light emission when intracellular calcium concentrations change. (Yong, Salzer, Grimbacher Immunol. Reviews 2009; Vol 229:101-113; Lindsey et al. Cytotherapy. 2007;9(2):123-32., Rabinowitz et al. Immunity, Volume 5, Issue 2, p125-135, 1 Aug. 1996).

Current in vitro assays to detect the costimulatory activity of a costimulatory ligand, for example B7RP1, on T cells have a number of limitations. First, the T cell must express the costimulatory receptor. In the case of ICOS, this can be problematic, since ICOS is not constitutively expressed by primary naïve T cells and most immortalized T cell lines. See, e.g., Yong et al. (2009), Immunol. Rev. 229: 101-113. Second, detectable activation of the T cells requires stimulation with both an anti-CD3 antibody and B7RP1, which complicates the practical execution of the assay. Third, given the requirement to co-stimulate with an anti-CD3 antibody, the ICOS-induced change in the selected read-out, e.g., IL-2, IL-10, or interferon gamma (IFN-γ) expression or cell proliferation, is often not large. See, e.g., FIG. 5 and Example 2 below; Zhang et al. (2011), Blood 118(11): 3062-3071; Chattopadhyay et al. (2006), J. Immunol. 177: 3920-3929. Such assays are not sensitive or robust because of this limited assay response range. Further, a limited response range can preclude the use of such assays to detect neutralizing anti-drug antibodies (Nabs), since this use normally requires at least about an 8-fold assay window at the level of ligand/receptor stimulation.

Two different kinds of assays for B7RP1 activity are illustrated in FIG. 1. The large squares with rounded corners represent T cells. The TCR-CD3 complex is represented by a pair of small filled rectangles, and ICOS is represented by a pair of small unfilled rectangles. A pair of rectangles that is mostly unfilled and partly filled represents a fusion protein comprising ICOS (unfilled region) plus a portion of the intracellular region of CD3 (filled region). An anti-CD3 antibody is represented by a plain Y-shaped figure, and a B7RP1-Fc protein is represented by Y-shaped figure in which the arms of the Y are elongated ovals. The arrows pointing from the TCR-CD3 complex (a dashed arrow) and from ICOS (a solid arrow) represent the intracellular signaling caused by engagement of these molecules leading to Akt activation which leads (dot-dash arrow) to either T cell activation (+) or a lack thereof (−) in situations where the TCR signaling pathway is not activated in cells expressing wildtype ICOS. The left-most two panels of FIG. 1 illustrate a situation where the T cell expresses both a TCR-CD3 complex and ICOS and thus requires stimulation by both anti-CD3 antibody and B7RP1-Fc for activation. The right-most two panels of FIG. 1 illustrate the situation described herein where the T cell expresses a TCR-CD3 complex (pair of small, filled rectangles) and a fusion protein comprising ICOS plus a portion of the intracellular region of CD3ζ (pair of small rectangle that is partly filled and partly unfilled). In this situation, stimulation by B7RP1-Fc alone is sufficient to activate the T cell, as illustrated in the right-most panel. As shown in the examples below, this assay provides a much enhanced signal for T cell activation, which is independent of anti-CD3 co-stimulation. See FIGS. 5-7 and Examples 2-4.

Figure 2C:
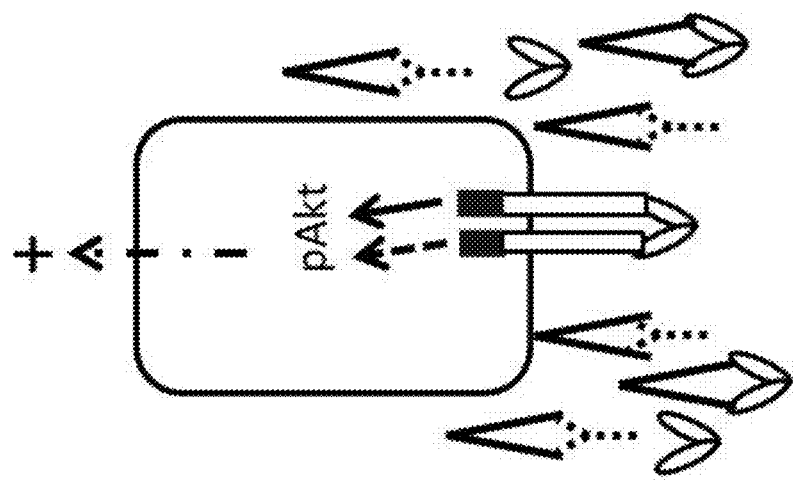
FIG. 2A, FIG. 2B and FIG. 2C: Diagrams of assays. The assays are designed to detect B7RP1 (FIG. 2A), a B7RP1 inhibitor (FIG. 2B), and an antibody that neutralizes a B7RP1 inhibitor (FIG. 2C). The large rectangles with rounded corners, the small vertical rectangles, the arrows, and the "+" and "−" signs have the same meaning indicated in the description of FIG. 1. All molecules added to the assay as part of the test sample being assayed are represented by shapes outlined with dotted lines, whereas molecules that are part of the assay mixture are represented by shapes outlined with solid lines.
Figure 2B:
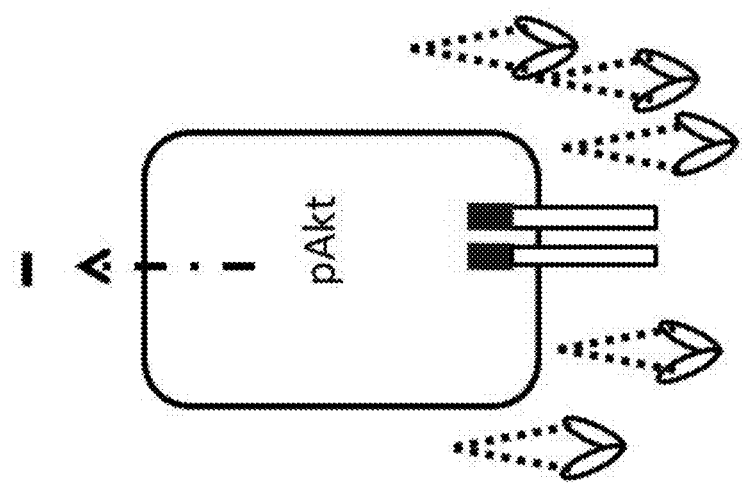
Figure 2A:
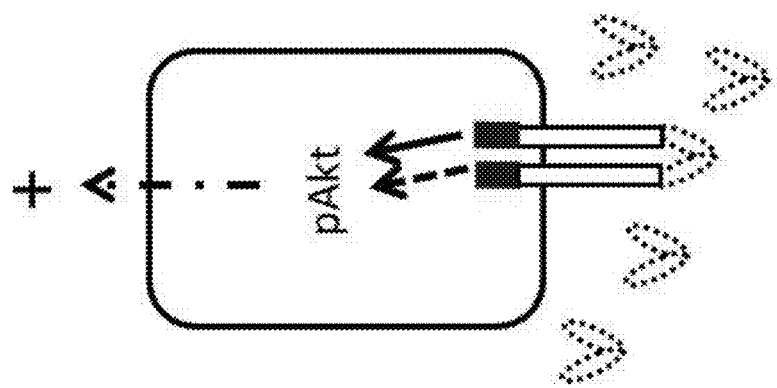

Some embodiments of the assays described herein are diagrammed in FIG. 2. T cells, the ICOS-CD3 fusion protein, and T cell activation are depicted as in FIG. 1. A V-shaped figure consisting of two elongated ovals represents dimeric B7RP1. The inverted V represents a B7RP1 inhibitor that inhibits the binding of B7RP1 to ICOS. The Y-shaped figure (consisting of dotted lines) in panel C is a molecule, e.g., an antibody, that binds to and neutralizes the B7RP1 inhibitor. The molecules depicted with dotted lines in each panel represent molecules being assayed that are added with the test sample. The molecules depicted with solid lines are part of the assay mixture. For example, in FIG. 2A, the assay is designed to detect B7RP1, which will activate the T cell. In FIG. 2B, the assay is designed to detect a B7RP1 inhibitor drug, which will block or inhibit T cell activation otherwise caused by B7RP1 that is part of the assay mixture. In FIG. 2C, the assay is designed to detect an anti-drug antibody that may develop in patients and binds to and neutralizes the B7RP1 inhibitor, which would otherwise block or inhibit T cell activation. Hence, the assays described herein can detect (1) a costimulatory ligand, such as B7RP1, B7-1, or B7-2, (2) an inhibitor of a costimulatory ligand, such as an inhibitor of B7RP1, B7-1, or B7-2, and (3) a molecule, e.g., an antibody, that can bind to and neutralize an inhibitor of a costimulatory ligand.

Fusion Proteins

Figure 3:
FIG. 3: A fusion protein. The fusion proteins described herein comprise, from amino- to carboxy-terminus, the following portions: part or all of the extracellular region of a costimulatory receptor, open rectangle; a transmembrane domain, solidly-filled rectangle; a sequence including a tyrosine-based signaling motif, where the sequence can include part or all the intracellular region of the costimulatory receptor, rectangle filled with vertical lines; and a sequence including a paired ITAM motif, where the sequence can include part or all of the intracellular region of a CD3 protein, rectangle filled with horizontal lines.

A fusion protein as described herein comprises at least (1) an extracellular region of a mammalian or avian costimulatory receptor, (2) a transmembrane domain, (3) an intracellular portion comprising a tyrosine-based signaling motif, which is optionally part of an intracellular portion of a mammalian or avian costimulatory receptor, and (4) an intracellular portion comprising a paired ITAM motif, which is optionally part of a mammalian or avian CD3 molecule, that is, CD3δ, CD3ε, CD3γ, and CD3ζ. This general structure is shown in FIG. 3. In some embodiments, all of these components can comprise, for example, mammalian or avian, e.g., human or murine, amino acid sequences.

The mammalian or avian costimulatory receptor can be an activating member of the CD28 family of costimulatory receptors, which includes CD28 and ICOS, or a polypeptide that is at least 90%, 95%, or 98% identical to CD28 or ICOS and that can mediate similar costimulatory activity when expressed on the surface of a T cell similar to that mediated by an unaltered CD28 or ICOS. See, e.g., Chattopadhyay et al. (2009), Immunol. Rev. 229(1): 356-386. These receptors are related in general structure, but are not closely related in sequence. The structure includes an extracellular immunoglobulin variable region-like (IgV-like) domain, followed by an extracellular stalk, followed by a transmembrane domain, followed by an intracellular region that comprises one or more tyrosine-based signaling motifs. Id. ICOS and CD28 are homodimers. Id. These receptors can be expressed on T cells. Upon engagement with their ligands, they become aggregated through cross-linking and deliver a positive signal that plays a role in inducing or enhancing T cell activation.

In Table 1 below, an alignment of the human and murine versions of ICOS and CD28 is shown. The alignment is designed to align the structural elements of the IgV-like regions of these molecules rather than only the sequence. See Chattopadhyay et al., (2009), Immunol. Rev. 229(1): 356-386. As is apparent from the alignment, the sequence similarity between different receptors, e.g., an ICOS vs. a CD28 receptor, is low. As indicated on the alignment, these sequences share certain key sequence similarities necessary for an IgV-like structure, although the overall sequence identity between ICOS and CD28, is low.

costimulatory ligand. Alternatively, the transmembrane domain of the fusion protein can be a transmembrane domain from a different protein or even a completely artificial transmembrane domain, provided that it is predicted to be a transmembrane domain by TMHMM software and provided that a T cell expressing the fusion protein can be activated (as measured by IL-2 secretion) in the presence of the corresponding costimulatory ligand.

A fusion protein as described herein contains a tyrosine-based signaling motif, for example, YMFM or YMNM, which can be part of a sequence containing all or part of the intracellular region of ICOS or CD28 or a sequence at least 90%, 95%, or 98% identical to such sequences, provided that the fusion protein retains biological activity. In this context, biological activity is the ability of a T cell having the fusion protein expressed on its surface to become activated by a costimulatory ligand as measured by secretion of at least three times as much IL-2 in the presence of an appropriate amount of a costimulatory ligand as is secreted in the absence of the costimulatory ligand.

A fusion protein as described herein also comprises a paired ITAM motif, which, optionally, can be part of an intracellular portion of a CD3 protein selected from among CD3ε, CD3ζ, CD3δ, and CD3γ or a protein that comprises

TABLE 1

Costimulatory Receptors

```
HICOS   eingsanyemfifhnggvqilCkypd..ivqqfkmqllkggqilcdltktkg.
MICOS   eingsadhrmfsfhnggvqisCkype..tvqqlkmrlfrerevlceltktkg.
HCD28   nkilvkqspmlvaydnavnlsCkysynlfsrefraslhkgldsavevcvvygn
MCD28    kilvkqspllvvdsnevslsCrysynllakefraslykgvnsdvevcvgngn
                                 ******

HICOS   ..sgntvsikslkfChsqlsnnsvsfflynldhshanyyfCnlsifdpppfk.vtltgg
MICOS   ..sgnaysiknpmlClyhlsnnsvsfflnnpdssqgsyyfCslsifdpppfqernlsgg
HCD28   ysqqlqvysktgfnCdgklgnesvtfylqnlyvnqtdiyfCkievmypppyldneksng
MCD28   ftyqpqfrsnaefnCdgdfdnetvtfrlwnlhvnhtdiyfCkiefmypppyldnersng HICOS   .ylhiyesqlCc......qlkfWLPIGCAAFVVVCILGCILICWLtkkkysssvhdpn
MICOS   .ylhiyesqlCc......qlklWLPVGCAAFVVVLLFGCILIIWFskkkygssvhdpn
HCD28   tiihvkgkhlCpsplfpgpskpfWVLVVVGGVLACYSLLVTVAFIIfwvrskrsrllh
MCD28   tiihikekhlChtqssp...klfwaLVVVAGVLFCYGLLVTVALCVIWtnsrrnrllg HICOS   geYMFMravntakksrltdvtl............51-179 of SEQ ID NO: 5
MICOS   seYMFMaavntnkksrlagvts........... 51-180 of SEQ ID NO: 18
HCD28   sdYMNMtprrpgptrkhyqpyapprdfaayrs..54-202 of SEQ ID NO: 6
MCD28   sdYMNMtprrpgltrkpyqpyapardfaayrp..53-198 of SEQ ID NO: 19
```

The asterisks above the second block of sequences indicate the position of a proline-rich motif important for ligand binding in CD28 and ICOS. The motifs shown in bold capital italic letters are tyrosine-based signaling motifs important for intracellular signaling. Cysteine residues are indicated with a boldface, underlined capital "C." Other conserved residues, or residues with similar properties, are indicated by lowercase, boldface, underlined letters. Transmembrance domains are indicated by capital, boldface letters.

As previously mentioned, ICOS and CD28 form homodimers, and a cysteine upstream from the transmembrane domain of these proteins (shown as a boldface, capital, underlined letter in Table 1) is known to be responsible for dimerization. See, e.g., Chattopadhyay et al. (2009), Immunol. Rev. 229(1): 356-386. A proline-rich sequence motif marked by asterisks in Table 1 is thought to be important for ligand binding in ICOS and CD28. Id.

The transmembrane domain portion of the fusion protein can, but need not, comprise exactly the same amino acid sequence as the transmembrane domain of the naturally occurring costimulatory receptor, for example ICOS or CD28. It can be at least 90% identical to the transmembrane domain of the costimulatory receptor, provided that a T cell expressing the fusion protein can be activated (as measured by IL-2 secretion) in the presence of the corresponding a sequence that is at least 90%, 95%, or 98% identical to the amino acid sequence of CD3ε, CD3ζ, CD3δ, and CD3γ, wherein the fusion protein is biologically active. In this context, biological activity is the ability of a T cell having the fusion protein expressed on its surface to become activated by a costimulatory ligand as measured by secretion of at least three times as much IL-2 in the presence of an appropriate amount of a costimulatory ligand as is secreted in the absence of the costimulatory ligand. As is known in the art, CD3 hetero- and/or homo-dimers mediate the intracellular signals that culminate in T cell activation when the TCR is engaged by its ligand. Id. An important factor in mediating these signals are the so-called paired ITAM motifs present in the intracellular regions of CD3ε, CD3ζ, CD3δ, and CD3γ. The paired ITAM motif has the structure YxxL/I-$X_{6-8}$-YxxL/I (where x is any amino acid, Y is tyrosine, and L/I means leucine or isoleucine), and the tyrosine residues are phosphorylated to initiate the signaling pathway that culminates in T cell activation. The CD3 protein can be from a mammalian or avian species, such as mouse, human, or chicken. CD3 proteins can form homo- or hetero-dimers with other CD3 proteins. For example, CD3ζ can form a homodimer, and CD3ε can form a heterodimer with either CD3γ or CD3δ. See, e.g., Kuhns and Badgandi (2012), Immunological Reviews 250: 120-143. A typical, fully-assembled TCR-CD3 complex comprises a CD3δε heterodimer, a CD3γε heterodimer, and a CD3ζζ homodimer in addition to a TCR αβ, pTαβ, or TCR δγ heterodimer. See, e.g., Kuhns and Badgandi (2012), Immunol. Rev. 250: 120-143. Residues in the transmembrane domain are important for dimerization of CD3ζ. See, e.g., Call et al. (2006), Cell 127(2): 355-368. For CD3ε, CD3δ, and CD3γ, a short sequence in the extracellular domains, i.e., R/KxCxxCxE (where x is any amino acid), has been implicated in the formation of CD3γε and CD3δε heterodimers. See, e.g., Rutledge et al. (1992), EMBO J. 11(9): 3245-3254; Kuhns and Badgandi (2012), Immunol. Rev. 250: 120-143.

In some embodiments, the fusion proteins described herein can comprise a portion of the intracellular region of a mammalian, optionally human or murine, CD3ε, CD3ζ, CD3δ, or CD3γ protein containing at least one paired ITAM motif. In some embodiments, this portion of an intracellular region can contain up to 1, 2, 3, 4, 5, 6, 7, 8, 9, or 10 substitutions, insertions or deletions of a single amino acid per 100 amino acids relative to the amino acid sequence of a wild type mammalian CD3ε, CD3ζ, CD3δ, or CD3γ, i.e., SEQ ID NO: 9, 8, 11, or 10, respectively. In some embodiments, the portion of the intracellular region can contain at least 1, 2, 3, 4, or 5 paired ITAM motifs and/or not more than 3, 4, 5, 6, 7, or 10 paired ITAM motifs. For example, the intracellular regions of CD3ε, CD3δ, and CD3γ each contain one paired ITAM motif. CD3ζ contains three paired motifs at residues 51-65, 90-105, and 121-135 of SEQ ID NO:8. A fusion protein can contain any one, two, or all three of the paired ITAM motifs in CD3ζ.

In some embodiments, the portion of the intracellular region of the CD3 protein may lack part or all or part of the region upstream from the first paired ITAM motif. For example, for human CD3ζ, the intracellular region has the amino acid sequence of residue 33-143 of SEQ ID NO:8, and the tyrosine residue of the first paired ITAM motif is at residue 51 of SEQ ID NO:8. A portion of the intracellular region of CD3ζ used in a fusion protein can lack residues 31-50 of SEQ ID NO:8 or can lack fewer of these amino acids. For example, the portion could lack residues 33-39 of SEQ ID NO:8 or could lack residues 33-34 of SEQ ID NO:8. Similarly, the intracellular regions of CD3δ, CD3ε, and CD3γ contain amino acids 107-150 of SEQ ID NO:11, amino acids 131-185 of SEQ ID NO:9, and amino acids 116-160 of SEQ ID NO:10, respectively. Portions of the intracellular regions of CD3δ, CD3ε, and CD3γ used in a fusion protein can lack amino acids 107-127 of SEQ ID NO:11, amino acids 131-165 of SEQ ID NO:9, and amino acids 116-137 of SEQ ID NO:10, respectively, or can lack a portion of these amino acid sequences.

Alternatively or in addition, the portion of the intracellular region of the CD3 protein can lack part or all of the region downstream from the last paired ITAM motif. For example, a portion of the intracellular region of CD3ζ used in a fusion protein can lack residues 136-143 of SEQ ID NO:8 or can lack part of this sequence. Similarly, the intracellular regions of CD3δ, CD3ε, and CD3γ can lack amino acids 143-150 of SEQ ID NO:11, amino acids 181-185 of SEQ ID NO:9, and amino acids 153-160 of SEQ ID NO:10, respectively, or can lack a portion of these sequences.

In more particular embodiments, a fusion protein can comprise the amino acid sequence of SEQ ID NO:12 or SEQ ID NO:14 or an amino acid sequence 90%, 95%, or 98% identical to either of these sequences provided that a T cell expressing the fusion protein can be induced to secrete at least three times as much IL-2 by a costimulatory ligand as it secretes in the absence of the costimulatory ligand.

Nucleic Acids and Vectors

Nucleic acids encoding any of the fusion proteins described herein are contemplated. For example, a nucleic acid encoding the fusion protein with SEQ ID NO:12 (ICOS-CD3 fusion III) is provided in SEQ ID NO:13, and a nucleic acid encoding the fusion protein with SEQ ID:14 is provided in SEQ ID NO:15 (ICOS-CD3 II). Any nucleic acid sequence encoding any amino acid sequence described herein is contemplated. As explained above, such fusion proteins include proteins that comprise exclusively amino acid sequences found in naturally-occurring proteins or, alternatively variant sequences that are at least 90%, 95%, or 98% identical to naturally-occurring sequences, wherein a T cell expressing the fusion protein can be induced to secrete at least three times as much IL-2 by a costimulatory ligand as it secretes in the absence of the costimulatory ligand.

Nucleic acid sequences encoding the fusion proteins described herein can be determined by one of skill in the art based on the amino acid sequences provided herein and knowledge in the art. Besides more traditional methods of producing cloned DNA segments encoding a particular amino acid sequence, companies such as DNA 2.0 (Menlo Park, Calif., USA) and BlueHeron (Bothell, Wash., USA), among others, now routinely produce chemically synthesized, gene-sized DNAs of any desired sequence to order, thus streamlining the process of producing such DNAs. Codon usage can be adjusted so as to optimize expression in the system of choice.

Nucleic acids encoding a fusion protein can be inserted into a vector suitable for introduction into a T cell, for example, a lentiviral vector or a retroviral vector. See, e.g., Verhoeyen et al., Lentiviral Vector Gene Transfer into Human T Cells, in GENETIC MODIFICATION OF HEMATOPOIETIC STEM CELLS, METHODS IN MOLECULAR BIOLOGY™, vol. 508, 2009, pp. 97-114.

Cell Lines

Cell lines used for the assays described in a general sense above and in detail in the Examples below express the fusion proteins described herein on their cell surface and also are T cells. A T cell can be a primary T cell isolated from a mammalian or avian species or an immortal cell line, for example, a leukemic cell line or a cell line from a lymphoma. Examples of commercially available human leukemic T cell lines include Mo (ATCC® CRL-8066™), C5/MJ (ATCC® CRL-8293™), and Jurkat (clone E6-1) (ATCC® TIB-152™). In the Examples below, Jurkat cells are used. The T cell can be transfected with nucleic acids encoding a fusion protein as described herein. In some embodiments, nucleic acids encoding a fusion protein are inserted into a lentiviral vector, which is used to produce viral particles, e.g., by transfection of the vector into packaging cells. Such procedures are described in Chen et al. (2012), Cell. Biochem. Biophys. 64: 233-240, the relevant portions of which are incorporated herein by reference. The viral particles containing nucleic acids encoding the fusion protein are used to transduce T cells. The nucleic acids can contain sequences necessary and/or helpful for expression of the fusion protein such as, for example, promoter sequences, enhancer sequences, ribosome start sites, etc. The lentiviral vector can comprise various promoters, for example, a cytomegalovirus promoter, a human elongation factor 1 α promoter, and a human phosphoglycerate kinase promoter, among many others. The T cell, when transfected or transduced with the nucleic acids encoding the fusion protein, can express the fusion protein. The transfected or transduced T cell can, but need not, also express the Ig superfamily costimulatory receptor that is part of the fusion protein on its cell surface.

The following examples are offered by way of exemplification and are not meant to limit the scope of the invention.

EXAMPLES

Example 1: Making ICOS-CD3ζ Nucleic Acids Encoding Fusion Proteins and Introducing them into Jurkat Cells DNA constructs encoding the ICOS-CD3ζ fusion proteins were generated by overlap PCR. See, e.g., Horton et al. (1989), Gene 77: 61-68, the portions of which explain how to perform PCR so as to unite fragments containing matching overhangs is incorporated herein by reference. Briefly, DNA fragments encoding full-length ICOS and portions of the intracellular region of CD3ζ were amplified in two separate PCR reactions using appropriate primers at the prospective fusion site that each contained a 5' overhang with the sequence of the respective fusion partner. The two PCR products were purified and mixed (without any primers) and subjected to several rounds of annealing/elongation cycles to allow overlap hybridization and extension. Subsequently, external primers (i.e. 5' ICOS primer and 3' CD3ζ primer) were added to amplify the fusion construct, which was ligated into a vector and introduced into bacteria for DNA amplification, clonal selection, and sequence verification.

DNAs encoding the ICOS-CD3ζ fusion proteins were shuttled via recombination (Gateway™ cloning technology sold by Life Technologies, Grand Island, N.Y., USA) into a lentiviral expression vector. The lentiviral vectors encoding the fusion proteins were transfected into the packaging cell line 293-6E. Viral supernatants were collected after 48 hours and used to infect Jurkat cells. Infected cells were selected based on their antibiotic resistance to puromycin (0.5 μg/mL), which was conferred by a selective marker encoded by the lentiviral vector.

Figure 4A:
FIG. 4A, FIG. 4B, and FIG. 4C: Diagrams of ICOS-CD3ζ fusion proteins.
Figure 4B:
Figure 4C:
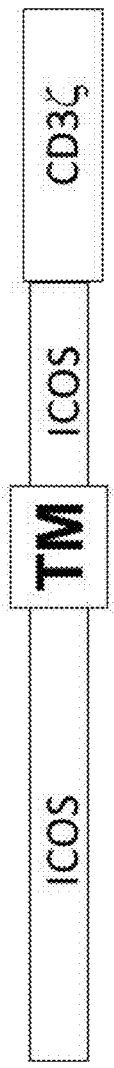

These fusion proteins are diagrammed in FIG. 4, where ICOS-CD3 I, ICOS-CD3 II, and ICOS-CD3 III are shown in FIG. 4A, FIG. 4B, and FIG. 4C, respectively. The filled rectangle in FIG. 4A represents the portion of the intracellular region of human CD3ζ that is immediately downstream from the transmembrane domain plus two amino acids within the transmembrane region of CD3ζ (amino acids 31-39 of SEQ ID NO:8). Following this, the remainder of the intracellular region of CD3ζ (i.e., amino acids 40-143 of SEQ ID NO:8) is shown as an open rectangle labeled "CD3ζ." In FIG. 4B and FIG. 4C, the open rectangle labeled "CD3ζ" has the same meaning. In FIG. 4B, the filled rectangle represents amino acids 35-39 of SEQ ID NO:8. ICOS-CD3 III, which is diagrammed in panel C, does not contain any amino acids 31-39 of SEQ ID NO:8. Thus, ICOS-CD3 I contains amino acid sequences immediately downstream from the transmembrane domain of CD3ζ and two amino acids within the transmembrane domain of CD3ζ. ICOS-CD3 II and III are missing 4 and 9 amino acids, respectively, from this region. Amino acid sequences for mature ICOS-CD3 I, ICOS-CD3 II, and ICOS-CD3 III are provided in SEQ ID NOs: 16, 14, and 12, respectively. Nucleic acid sequences encoding these fusion proteins are provided in SEQ ID NOs: 17, 15, and 13, respectively.

Example 2: Testing T Cells Expressing ICOS-CD3 Fusion Proteins for Activation

The following experiments were done to determine whether cells expressing the fusion proteins described in Example 1 could be activated when stimulated with an anti-CD3 antibody plus a B7RP1-Fc protein. Round-bottom 96-well plates were coated at 4° C. overnight with 50 μl/well of PBS containing anti-human IgG capture antibody and anti-CD3 antibody. The plate was washed three times with PBS and then coated at ambient temperature for 3 hours with 50 μl/well of PBS containing B7RP1-Fc protein. B7RP1-Fc fusion protein can be purchased from, e.g., R & D Systems of Minneapolis, Minn. (Recombinant Human B7-H2 Fc Chimera, Catalog No. 165-B7-100). The plate was then washed three times with PBS and 50,000 Jurkat cells expressing ICOS, ICOS-CD3 I, ICOS-CD3 II, or ICOS-CD3 III were plated in 200 μl RPMI growth medium in each well. Each sample was run in triplicate. IL-2 secretion was measured in cell culture supernatants after 72 hours with the Meso Scale Discovery (MSD) IL-2 Tissue Culture kit.

Figure 5:
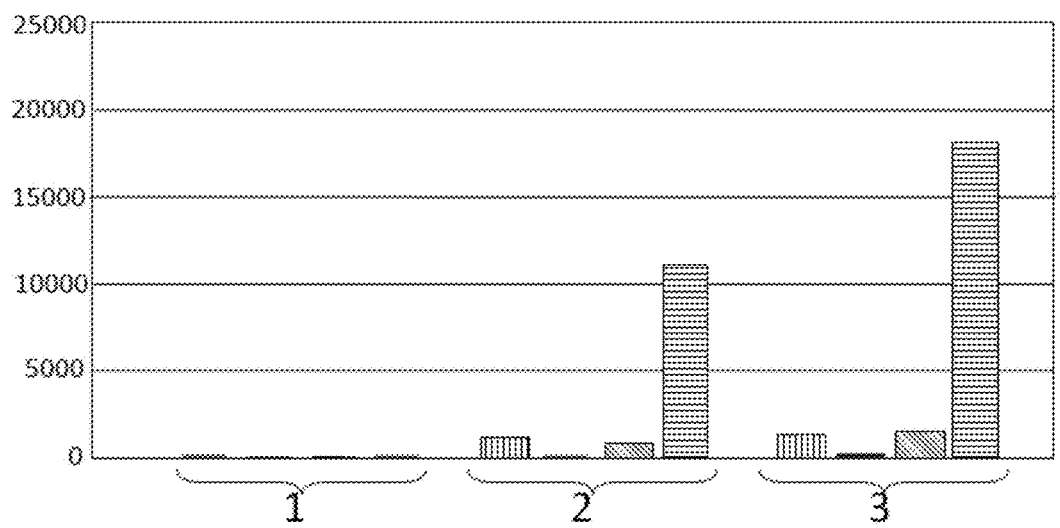
FIG. 5: Activation of T cells by B7RP1-Fc and anti-CD3 antibody. The graph shows three clusters of four samples, which represent data from samples that were stimulated with 2.5 μg/mL anti-CD3 antibody alone (1), 2.5 μg/mL anti-CD3 antibody plus 5 μg/mL B7RP1-Fc (2), or 2.5 μg/mL anti-CD3 antibody plus 50m/mL B7RP1-Fc (3). The y axis indicates relative levels of IL-2 secretion (relative luminescence units, RLUs). The four different kinds of samples in each cluster contained cells expressing, from left to right, the following molecules: wild type human ICOS, ▥ ; ICOS-CD3 I, ▪; ICOS-CD3 II, ▨; ; and ICOS-CD3 III, ▤. . The difference between levels of IL-2 in clusters 1 and 3 in samples containing cells expressing wild type ICOS was less than eight fold and in samples containing cells expressing ICOS-CD3 III was more than 200 fold.

The results are shown in FIG. 5. FIG. 5 shows data from three groups of samples. Each group contains data from samples, which were, from left to right, stimulated with the following proteins: (1) 2.5 μg/mL anti-CD3 antibody alone; (2) 2.5 μg/mL anti-CD3 antibody plus 5 μg/mL B7RP1-Fc; or (3) 2.5 μg/mL anti-CD3 antibody plus 50 μg/mL B7RP1-Fc. Each of groups (1)-(3) contains data from four samples, which, from left to right, contained cells expressing the following receptors: wild type human ICOS, ; ICOS-CD3 I, ; ICOS-CD3 II, ; and ICOS-CD3 III, . These data show that the cells expressing ICOS-CD3 III produced far more IL-2 in response stimulation with anti-CD3 antibody and B7RP1-Fc than cells expressing either wild type ICOS, ICOS-CD3 I, or ICOS-CD3 II. Further, these data indicate that cells expressing ICOS-CD3 III produced more than 170 times more IL-2 when stimulated with 2.5 μg/mL anti-CD3 antibody plus 50 μg/mL B7RP1-Fc (group 3 conditions) than they did when stimulated with 2.5 μg/mL anti-CD3 antibody alone (group 1 conditions). In contrast, cells expressing wild type ICOS had an increase in IL-2 secretion of less than seventeen fold in the group 3 conditions, as compared to the group 1 conditions. Cells expressing ICOS-CD3 II behaved similarly to cells expressing wild type ICOS, and cells expressing ICOS-CD3 I showed no increase in IL-2 secretion in the group 3 or group 2 conditions compared to the group 1 conditions. Hence, these data demonstrate that cells expressing wildtype ICOS or ICOS-CD3 II and III fusion proteins can be activated by anti-CD3 and B7RP1-Fc stimulation to secret IL-2. In contrast, cells expressing ICOS-CD3 I, which contains two amino acids of the transmembrane portion of CD3ζ, could not be activated to secret IL-2 under the same conditions. Cells expressing ICOS-CD3 III secreted the most IL-2 under group 2 and 3 conditions, and thus these cells were selected for further characterization.

Example 3: Testing T Cells Expressing ICOS-CD3 III for Activation by B7RP1-Fc in the Absence of Anti-CD3 Stimulation To determine whether T cells expressing ICOS-CD3 III can be activated by B7RP1 in the absence of anti-CD3, cells expressing ICOS-CD3 III or wild type ICOS were tested for their response to varying levels of B7RP1-Fc alone in a T cell activation assay.

To perform the T cell activation assays, round-bottom 96-well plates were coated at 4° C. overnight with 50 µl/well of PBS containing 10 ug/mL of an anti-human IgG capture antibody but no anti-CD3 antibody. The plates were washed three times with PBS and then coated at room temperature for 3 hours with 50 µl/well of PBS containing varying amounts of B7RP1-Fc protein. The plates were then washed three times with PBS and 50,000 Jurkat cells expressing ICOS or ICOS-CD3 III in 200 µl RPMI growth medium were deposited in each well. Each sample was run in duplicate. IL-2 secretion was measured in cell culture supernatants after 72 hours of incubation with the Meso Scale Discovery (MSD) IL-2 Tissue Culture kit.

Figure 6:
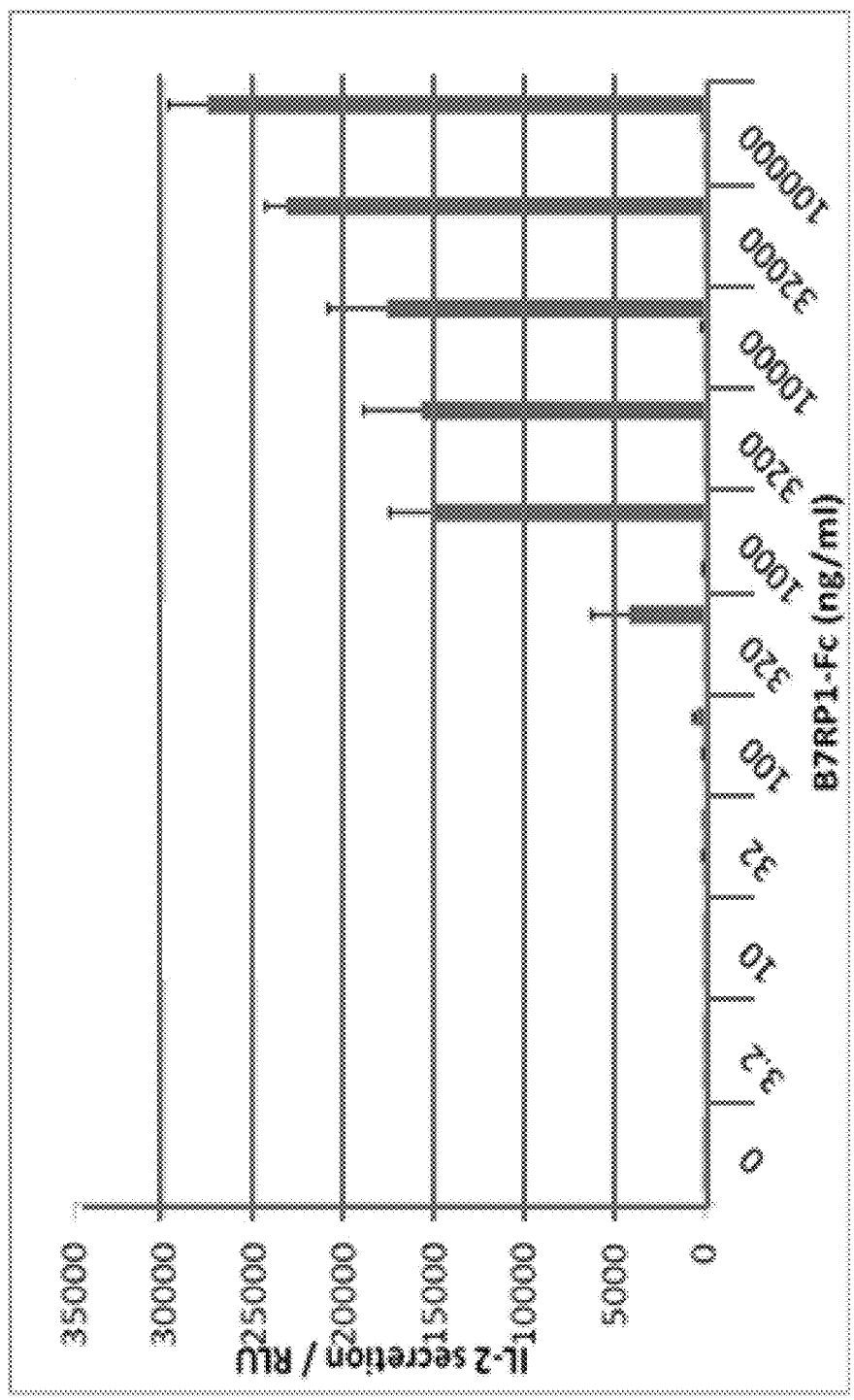
FIG. 6: Response to varying doses of B7RP1-Fc by cells expressing the ICOS-CD3 III fusion protein. As indicated, the y axis indicates the levels of IL-2 secreted by the cells. As indicated across the x axis, cell supernatants from cells exposed to varying doses of B7RP1-Fc, ranging from 0-100, 000 ng/mL, were tested. The figure shows data from four different kinds of cells at each dose level, which are from left to right: Jurkat cells transfected with an empty vector; Jurkat cells transfected with a vector encoding full length human wild type ICOS (derived from frozen vial 1); Jurkat cells transfected with a vector encoding full length human wild type ICOS (derived from frozen vial 2); and non-clonal Jurkat cells transfected with a vector encoding the ICOS-CD3 III fusion protein. As is apparent in the figure, only cells expressing the ICOS-CD3 III fusion protein, i.e., the right-most bar at each dose level indicated, secreted appreciable amounts of IL-2 in response to B7RP1-Fc in the absence of an anti-CD3 antibody.

Results are shown in FIG. 6. The amount of B7RP1-Fc used in each sample is indicated along the x axis in FIG. 6. The following four different kinds of cells, from left to right, were tested with each amount of B7RP1-Fc: Jurkat cells transfected with an empty vector; Jurkat cells transfected with a vector encoding full length human wild type ICOS (derived from frozen vial 1); Jurkat cells transfected with a vector encoding full length human wild type ICOS (derived from frozen vial 2); and non-clonal Jurkat cells transfected with a vector encoding the ICOS-CD3 III fusion protein. These results show that Jurkat cells expressing ICOS-CD3 III, but not wild type ICOS, respond to increasing levels of B7RP1-Fc with increasing levels of IL-2 secretion, thus showing that stimulation with B7RP1 alone, in the absence of anti-CD3 stimulation, is sufficient to activate T cells expressing ICOS-CD3 III.

Example 4: Selection and Testing of Clonal T Cell Lines Expressing ICOS-CD3 III

To obtain a stable cell line expressing ICOS-CD3 III or wild type ICOS, clonal cell lines of Jurkat cells expressing ICOS-CD3 III were derived using the method of limiting dilution. Briefly, viable Jurkat cells expressing ICOS-CD3 III or wild type human ICOS were counted with a ViCell® Cell Viability Analyzer (Beckman Coulter, Inc.) and diluted to a density of 0.3 cells/well in 200 µl of growth medium in several 96-well round-bottom plates. After approximately 3-4 weeks of growth in a standard tissue culture incubator, single-cell clones were identified by visual inspection To determine whether clonal cells expressing ICOS-CD3 III can be activated by B7RP1 in absence of anti-CD3 stimulation, two clonal cell lines (designated B5 and C7) were tested for their response to varying levels of B7RP1-Fc in a T cell activation assay and compared to parental, non-clonal population of cells expressing ICOS-CD3 III. To perform the T cell activation assays, round-bottom 96-well plates were coated at 4° C. overnight with 50 µl/well of PBS containing 10 µl/mL of an anti-human IgG capture antibody but no anti-CD3 antibody. The plate was washed three times with PBS and then coated at room temperature for 3 hours with 50 µl/well of PBS containing varying amounts of B7RP1-Fc protein. The plates were then washed three times with PBS and 50,000 Jurkat cells expressing ICOS-CD3 III in 200 µl RPMI growth medium were deposited in each well. Each sample was run in duplicate. IL-2 secretion was measured in cell culture supernatants after 72 hours of incubation with the Meso Scale Discovery (MSD) IL-2 Tissue Culture kit.

Figure 7:
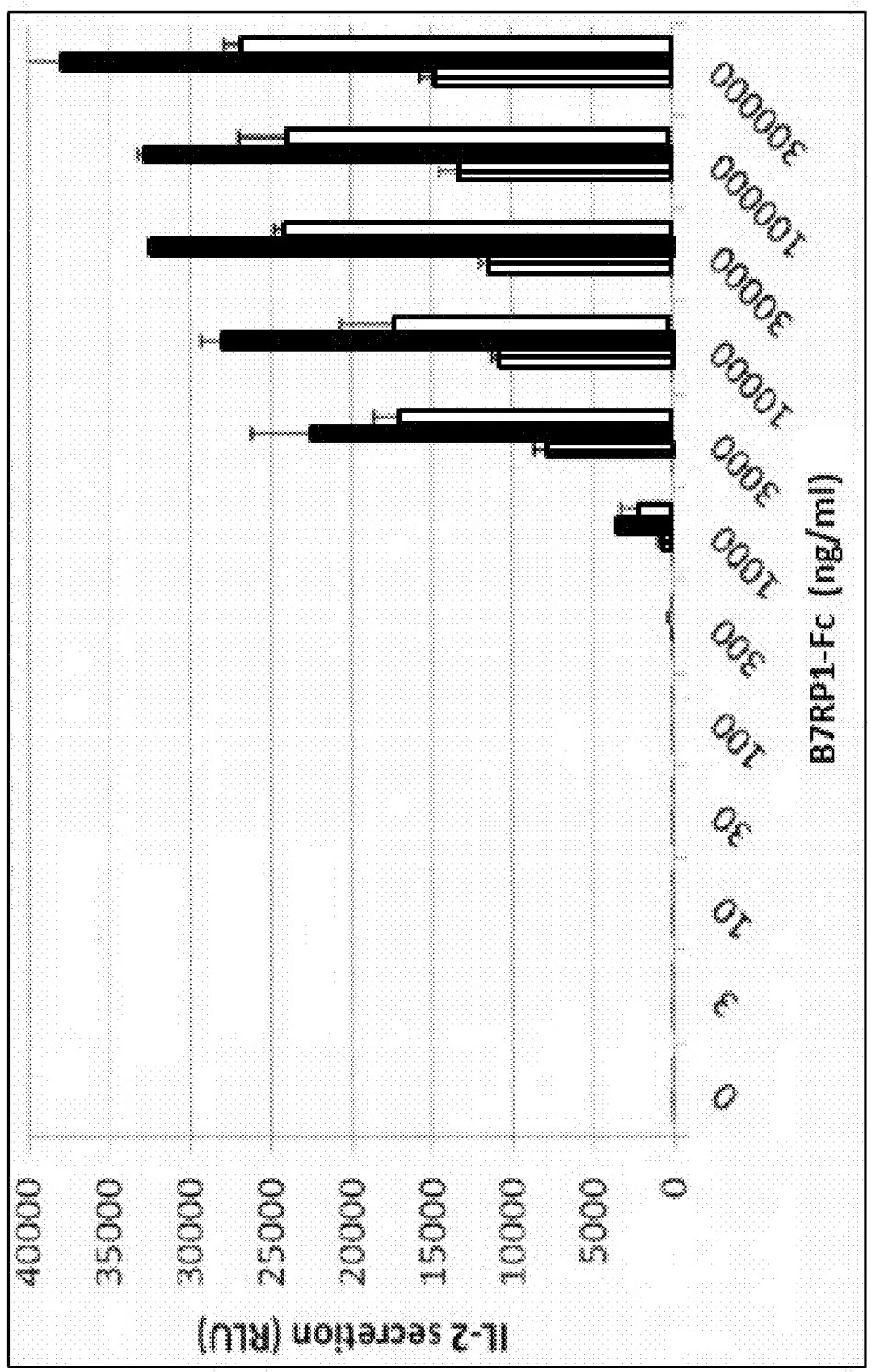
FIG. 7: Levels of IL-2 secretion in response to B7RP1-Fc by different cell lines expressing ICOS-CD3 III. As indicated, the y axis shows the relative levels of IL-2 secreted, and the x axis indicates the levels of B7RP1-Fc used in the assay. No anti-CD3 antibody was added to the assay. At each level of B7RP1-Fc, the following four different kinds of cells were used (from left to right): Jurkat cells transfected with an empty-vector (EV control), ▤; ; a non-clonal population of Jurkat cells transfected with ICOS-CD3III, ▯; ; a clonal cell line (B5) transfected with ICOS-CD3 III, ▪; and another clonal cell line (C7) transfected with ICOS-CD3 III, ▯.

Results are shown in FIG. 7. Levels of B7RP1-Fc used in the assays are indicated along the x axis of FIG. 7. At each level of B7RP1-Fc, the following four different kinds of cells were used (from left to right): Jurkat cells transfected with an empty-vector (EV control), ▬; ; a non-clonal population of Jurkat cells transfected with ICOS-CD3 III, □; ; a clonal cell line (B5) transfected with ICOS-CD3 III, ■; and another clonal cell line (C7) transfected with ICOS-CD3 III, □. These data demonstrate that both the B5 and C7 clonal Jurkat cell lines expressing ICOS-CD3 III were more responsive to stimulation with B7RP1-Fc than a non-clonal population of Jurkat cells expressing ICOS-CD3 III. The B5 cell line exhibited the highest amount of IL-2 secretion among the cell lines tested at all levels of B7RP1-Fc that were high enough to elicit appreciable IL-2 secretion. These data demonstrate that selection of particular clonal lines can significantly improve the assay response when utilizing such cell lines to detect activation of T cells by B7RP1-Fc.

Example 5: Inhibition of Response to B7RP1-Fc by an Antagonistic Anti-B7RP1 Antibody In the experiment described below, varying amounts of an antagonistic anti-B7RP1 antibody (referred to as "the anti-B7RP1 antibody drug") were added to T cell activation assays using the clonal cell line B5 described above (which expresses ICOS-CD3 III) stimulated with a constant amount of B7RP1-Fc. Round-bottom 96-well microtiter plates were coated at 4° C. overnight with 50 µl/well of 5 µg/mL anti-B7RP1 capture antibody in PBS. No anti-CD3 antibody was added. The plate was washed three times with PBS and then coated at room temperature for 3 hours with 50 µl/well of B7RP1-Fc at a concentration of 1 µg/mL in PBS. The plates were then washed three times with PBS, and 100 µl of culture medium containing varying amounts of the anti-B7RP1 antibody drug were added to each well. Plates were incubated for 30 minutes at room temperature. Subsequently, 100 µl of culture medium containing about 200,000 Jurkat cells expressing ICOS-CD3 III (clonal cell line B5) were added to each well. In addition, a final concentration of 10% Pooled Human Normal Serum (PNS) was added to mimic to matrix of potential future test samples. Each sample was run in duplicate. IL-2 secretion was measured in cell culture supernatants after 20 hours using the Meso Scale Discovery (MSD) IL-2 Tissue Culture kit.

Figure 8:
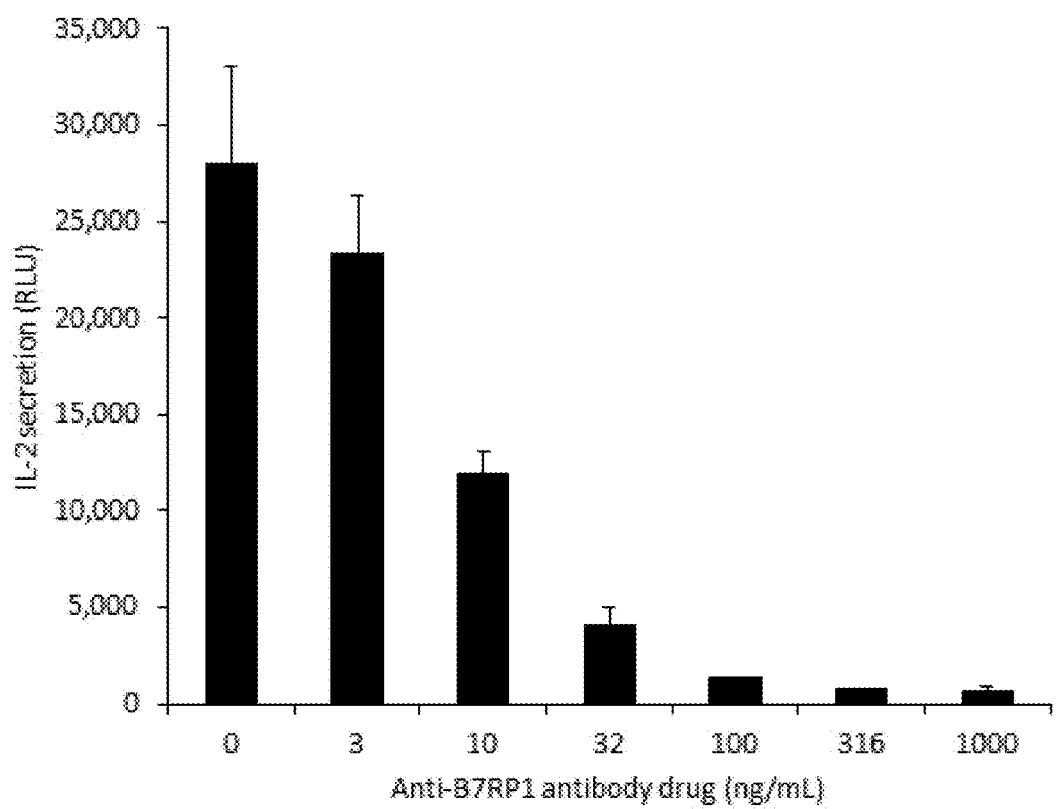
FIG. 8: Response to varying doses of an inhibitory anti-B7RP1 antibody in the presence of B7RP1-Fc by cells expressing ICOS-CD3 III (clonal cell line B5). As indicated, the y axis shows relative levels of IL-2 detected in the cell supernatant, and the x axis indicates the concentration of an inhibitory anti-B7RP1 antibody used in each sample.

Results are shown in FIG. 8. Data are displayed as bars representing the relative levels of IL-2 detected. Final concentrations of the anti-B7RP1 antibody drug used in the wells of the microtiter plate are indicated along the x axis of FIG. 8. These data show that T cell activation in response to B7RP1-Fc detected in the assay described above can be inhibited in a dose dependent manner by the anti-B7RP1 antibody drug. The $IC_{50}$ value for the anti-B7RP1 antibody drug was about 9 ng/mL, as determined by 4-point nonlinear regression analysis of logarithmically transformed data, using GraphPad Prism software Version 6.03. Thus, assays described herein can be adapted to detect inhibitors of B7RP1.

Example 6: Detection of Antibodies that Neutralize an Antagonistic Anti-B7RP1 Antibody The following experiment illustrates that a T cell line expressing ICOS-CD3 III can be used to detect antibodies that block the anti-B7RP1 antibody drug (i.e., "neutralizing anti-drug antibodies"). Round-bottom 96-well microtiter plates were coated at 4° C. overnight with 50 µl/well of 5 ug/mL anti-B7RP1 capture antibody in PBS. The plate was washed three times with PBS and then coated at room temperature for 3 hours with 50 µl/well of B7RP1-Fc at a concentration of 1 µg/mL in PBS. The plate was then washed three times with PBS, and 100 µl of culture medium containing about 2×10$^5$ Jurkat cells expressing ICOS-CD3 III (clonal cell line B5) and 30 ng/mL of the anti-B7RP1 antibody drug. In addition, varying amounts of a polyclonal antibody preparation that can neutralize the anti-B7RP1antibody drug (anti-drug antibodies) were added to each well, together with either 10% pooled human normal serum (PNS) or 10% pooled human systemic lupus erythematosus serum (PLS), which represent the matrix of potential future test samples. Plates were incubated for 30 min at room temperature. IL-2 secretion was measured in cell culture supernatants after one day using the Meso Scale Discovery (MSD) IL-2 Tissue Culture kit.

Figure 9A:
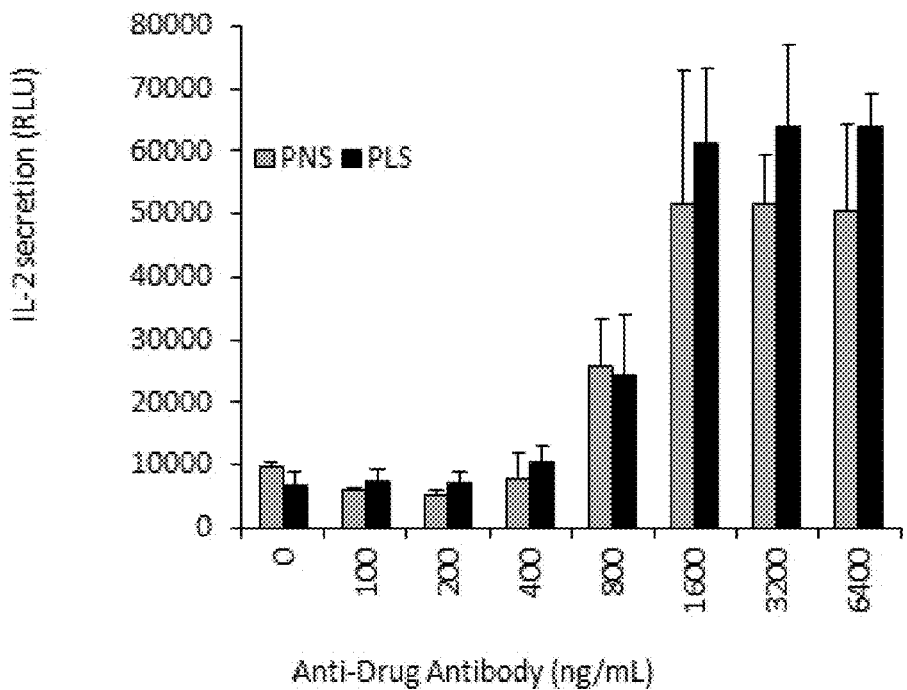
FIG. 9A: Detection of neutralizing anti-drug antibodies. As indicated, the y axis shows levels of IL-2 secreted by the cells in each sample, and the x axis shows the concentration of a polyclonal antibody preparation (Anti-Drug Antibody) that can neutralize the inhibitory anti-B7RP1 antibody drug. The solidly-filled black rectangles represent data from assays that contained 10% pooled human serum from systemic lupus erythematosus (SLE) patients (PLS), and the solidly-filled grey rectangles represent data from assays that contained 10% pooled normal human serum (PNS). Methods are explained in Example 6.
Figure 9B:
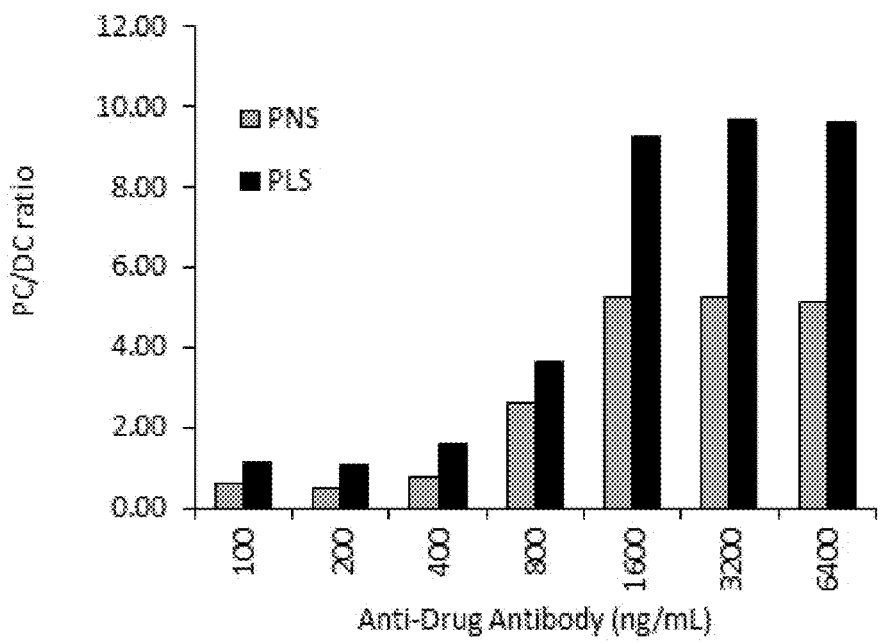
FIG. 9B: Relative response window for detection of anti-drug antibodies. The x axis and the solidly-filled black and grey rectangles indicate as explained in the description of FIG. 9A. The y axis indicates the PC/DC ratio, which is the ratio of the amount of IL-2 detected with the indicated level of anti-drug antibody divided by the amount of IL-2 detected when no anti-drug antibody is present. Methods are explained in Example 6.

The results are shown in FIGS. 9A and 9B. FIG. 9A shows that secretion of IL-2 increases with increasing concentrations of anti-drug antibodies in a dose-dependent manner. Curve fitting through 4-point nonlinear regression of logarithmically transformed data using GraphPad Prism software Version 6.03 determined an $EC_{50}$ value for the anti-drug antibody of about 830 ng/mL in PNS and about 950 ng/mL in PLS.

In FIG. 9B, the assay response window ("PC/DC" ratio) was calculated by dividing the levels of IL-2 detected using the various amounts of anti-drug antibodies with the levels of IL-2 detected with no anti-drug antibodies added to the assay. Compared to levels of IL-2 detected in the absence of the anti-drug antibodies, almost 10 times (in PLS) or 5 times (in PNS) more IL-2 was produced at the highest levels of anti-drug antibodies tested. To perform reliably during production, neutralizing anti-drug antibody assays should have an assay response window of at least 2 to 3-fold. Therefore, these data show that the assay meets the minimal requirements for neutralizing anti-drug antibody assays and thus can be used to detect the presence of neutralizing anti-drug antibodies in test samples from human subjects that were dosed with an antagonistic anti-B7RP1 antibody, such as the anti-B7RP1 antibody drug used here.

---

What is claimed is:

1. A fusion protein comprising the following polypeptides:
   (a) an extracellular region of a costimulatory receptor comprising amino acids 1-121 of SEQ ID NO:5 or amino acids 1-135 of SEQ ID NO:6;
   (b) a transmembrane domain comprising amino acids 122-144 of SEQ ID NO:5 or amino acids 136-158 of SEQ ID NO:6;
   (c) an intracellular region of the costimulatory receptor, which comprises at least one tyrosine-based signaling motif having the amino acid sequence of Tyr-Met-Phe-Met (SEQ ID NO:2) when the extracellular region is amino acids 1-121 of SEQ ID NO:5, or Tyr-Met-Asn-Met (SEQ ID NO:1) when the extracellular region is amino acids 1-135 of SEQ ID NO:6; and
   (d) an intracellular region of a CD3 protein that comprises at least one paired ITAM motif, wherein the intracellular region of the CD3 protein comprises amino acids 138-152 of SEQ ID NO:10, amino acids 138-160 of SEQ ID NO:10, amino acids 166-180 of SEQ ID NO:9, amino acids 128-142 of SEQ ID NO:11, amino acids 51-65 of SEQ ID NO:8, amino acids 90-105 of SEQ ID NO:8, amino acids 121-135 of SEQ ID NO:8, or amino acids 51-135 of SEQ ID NO:8,
   wherein a T cell expressing the fusion protein can be induced to secrete at least three times as much IL-2 by a costimulatory ligand as it secretes in the absence of the costimulatory ligand.

2. The fusion protein of claim 1, wherein the intracellular region of (c) comprises the amino acid sequence of Tyr-Met-Phe-Met (SEQ ID NO:2) and an amino acid sequence at least 90% identical to amino acids 145-179 of SEQ ID NO:5.

3. The fusion protein of claim 1, wherein the intracellular region of (c) comprises the amino acid sequence of amino acids 159-202 of SEQ ID NO:6.

4. The fusion protein of claim 1, wherein the transmembrane domain of (b) comprises the amino acid sequence of amino acids 122-144 of SEQ ID NO:5.

5. The fusion protein of claim 1, wherein the transmembrane domain of (b) comprises the sequence of amino acids 136-158 of SEQ ID NO:6.

6. The fusion protein of claim 1, wherein the intracellular region of the CD3 protein comprises the sequence of amino acids 138-152 of SEQ ID NO:10.

7. The fusion protein of claim 6, wherein the CD3 protein is human CD3γ.

8. The fusion protein of claim 7, wherein the intracellular region of the CD3 protein comprises amino acids 138-160 of SEQ ID NO:10.

9. The fusion protein of claim 1, wherein the intracellular region of the CD3 protein comprises the sequence of amino acids 166-180 of SEQ ID NO:9.

10. The fusion protein of claim 9, wherein the CD3 protein is human CD3ε.

11. The fusion protein of claim 1, wherein the intracellular region of the CD3 protein comprises the sequence of amino acids 128-142 of SEQ ID NO:11.

12. The fusion protein of claim 11, wherein the CD3 protein is human CD3δ.

13. The fusion protein of claim 1, wherein the intracellular region of the CD3 protein comprises the sequence of amino acids 51-65 of SEQ ID NO:8.

14. The fusion protein of claim 1, wherein the intracellular region of the CD3 protein comprises the sequence of amino acids 90-105 of SEQ ID NO:8.

15. The fusion protein of claim 1, wherein the intracellular region of the CD3 protein comprises the sequence of amino acids 121-135 of SEQ ID NO:8.

16. The fusion protein of claim 1, wherein the CD3 protein is human CD3ζ.

17. The fusion protein of claim 16, wherein the intracellular region of the CD3 protein comprises the sequence of amino acids 51-135 of SEQ ID NO:8.

18. A fusion protein comprising the amino acid sequence of SEQ ID NO:12.

19. A fusion protein comprising the amino acid sequence of SEQ ID NO:14.

20. A nucleic acid encoding a fusion protein of claim 1.

21. An isolated T cell comprising the nucleic acid of claim 20.

22. The isolated T cell of claim 21, which is from a T cell lymphoma cell line or a T cell leukemia cell line.

23. A method for determining the concentration of a bioactive costimulatory ligand in a test sample comprising:
  (a) providing T cells that express the fusion protein of claim 1;
  (b) determining the level of a signal indicating T cell activation in the following kinds of samples comprising the T cells of (a):
    (1) in the absence of both the test sample and the costimulatory ligand,
    (2) in the presence of varying concentrations of the test sample, and
    (3) in the presence of varying known concentrations of the costimulatory ligand; and
  (c) comparing the signals detected in the presence of varying concentrations of the test sample with those detected in the presence of varying levels of costimulatory ligand, thereby determining the concentration of the bioactive costimulatory ligand in the test sample.

24. The method of claim 23, wherein the one or more signals determined in (b) are from an assay for IL-2 secreted by the T cells.

25. (A method for determining the concentration of a bioactive inhibitor of a costimulatory ligand in a test sample comprising:
  (a) providing T cells that express the fusion protein of claim 1;
  (b) determining the level of a signal indicating T cell activation in the following kinds of samples comprising the T cells of (a):
    (1) in the absence of the test sample and in the presence of a constant amount of the costimulatory ligand sufficient such that the signal produced by the T cells is at least twice as large as it is in the absence of the costimulatory ligand,
    (2) in the presence of the constant amount of the costimulatory ligand and varying concentrations of the test sample, and
    (3) in the presence of the constant amount of the costimulatory ligand and varying known concentrations of the inhibitor; and
  (c) comparing the signals determined in (b)(2) with those detected in (b)(3) to determine the concentration bioactive inhibitor in the test sample.

26. The method of claim 25, wherein the amount of the costimulatory ligand in step (b) is sufficient to induce the T cells to produce a signal at least four times as large as they produce in the absence of the costimulatory ligand.

27. The method of claim 25, wherein the one or more signals are from an assay for IL-2 secreted by the T cells.

28. A method for determining the presence of antibodies that neutralize an inhibitor of a costimulatory ligand in a test sample comprising:
  (a) providing T cells that expresses the fusion protein of claim 1;
  (b) determining the level of a signal indicating T cell activation in the following kinds of samples comprising the T cells of (a):
    (1) in the presence of constant concentrations of both the costimulatory ligand and the inhibitor, wherein the constant concentration of the costimulatory ligand is sufficient, in the absence of the inhibitor, to induce the T cells to produce a signal at least five times as large as they produce in the absence of the costimulatory ligand, wherein the constant concentration of the inhibitor is sufficient, in the presence of the constant concentration of the costimulatory ligand, to provide at least a three-fold reduction in the signal;
    (2) in the presence of the constant concentrations of both the costimulatory ligand and the inhibitor of the costimulatory ligand and in the presence of a known concentration of one or more antibodies that neutralize the inhibitor; and
    (3) in the presence of the constant concentrations of both the costimulatory ligand and the inhibitor of the costimulatory ligand and in the presence of a test sample; and
  (c) comparing the signals obtained in (b)(2) and (b)(3), each normalized to the value obtained in (b)(1), to determine the presence of antibodies in the test sample that neutralize the inhibitor.

29. The method of claim 28, wherein the one or more signals are from an assay for IL-2 secreted by the T cells.

30. A nucleic acid encoding the fusion protein of claim 18.

31. An isolated T cell comprising the nucleic acid of claim 30.

32. The isolated T cell of claim 31, which is from a T cell lymphoma cell line or a T cell leukemia cell line.

33. A nucleic acid encoding the fusion protein of claim 19.

34. An isolated T cell comprising the nucleic acid of claim 33.

35. The isolated T cell of claim 34, which is from a T cell lymphoma cell line or a T cell leukemia cell line.

* * * * *

UNITED STATES PATENT AND TRADEMARK OFFICE
CERTIFICATE OF CORRECTION

PATENT NO. : 10,047,138 B1
APPLICATION NO. : 14/956787
DATED : August 14, 2018
INVENTOR(S) : Christian Vettermann It is certified that error appears in the above-identified patent and that said Letters Patent is hereby corrected as shown below:

In the Specification

Column 4, Line 67, "51-135of" should read -- 51-135 of --.

Column 6, Line 27, "ICOS-CD3fusion" should read -- ICOS-CD3 fusion --.

Column 7, Line 58, "50m/mL" should read -- 50 µg/mL --.

Column 7, Line 63, "; ; and ICOS-CD3 III, . ." should read -- ; and ICOS-CD3 III, . --.

Column 8, Line 26, "; ;" should read -- ; --.

Column 8, Line 27, "ICOS-CD3III, ; ;" should read -- ICOS-CD3 III, ; --.

Column 11, Line 51, "αβPTCR" should read -- αβTCR --.

Column 11, Line 53, "CD3ζproteins" should read -- CD3ζ proteins --.

Column 11, Lines 65-66, "fluoresecently" should read -- fluorescently --.

Column 12, Line 21, "Affimetrix" should read -- Affymetrix --.

Column 12, Lines 29-30, "phosphorylatation" should read -- phosphorylation --.

Signed and Sealed this
Thirty-first Day of December, 2019

Andrei Iancu
*Director of the United States Patent and Trademark Office*

CERTIFICATE OF CORRECTION (continued)
U.S. Pat. No. 10,047,138 B1

Column 15, Line 17, "Affimetrix" should be -- Affymetrix --.

Column 15, Line 18, "2below." should read -- 2 below. --.

Column 15, Line 24, "phosphorylatation" should read -- phosphorylation --.

Column 15, Line 66, "of CD3" should read -- of CD3ζ --.

Columns 17 & 18, below Table 1 "Transmembrance" should read -- Transmembrane --.

Column 22, Line 35, "; ; and ICOS-CD3 III, 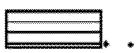. ." should read -- ; and ICOS-CD3 III, 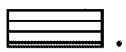. --.

Column 23, Line 46, "inspection" should read -- inspection. --.

Column 23, Line 55, "10 μl/mL" should read -- 10 μg/mL --.

Column 24, Line 3, "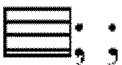; ;" should read -- ; --.

Column 24, Line 4, "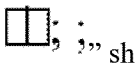; ;" should read -- ; --.

Column 25, Lines 7-8, "anti-B7RP1antibody" should read -- anti-B7RP1 antibody --.

Columns 25 & 26, under "Sequence Listing", Line 7, "Synethetic" should read -- Synthetic --.

In the Claims

Column 50, Lines 41-43, "comprises the amino acid sequence of Tyr-Met-Phe-Met (SEQ ID NO:2) and an amino acid sequence at least 90% identical to amino" should read -- comprises amino --.

Column 51, Line 50, "(A method" should read -- A method --.

SEQUENCE LISTING

```
<160> NUMBER OF SEQ ID NOS: 21

<210> SEQ ID NO 1
<211> LENGTH: 4
<212> TYPE: PRT
<213> ORGANISM: Artificial Sequence
<220> FEATURE:
<223> OTHER INFORMATION: Synethetic Polypeptide
<220> FEATURE:
<221> NAME/KEY: MISC_FEATURE
<223> OTHER INFORMATION: Tyrosine-based signaling motif

<400> SEQUENCE: 1

Tyr Met Asn Met
1

<210> SEQ ID NO 2
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Tyrosine-based motif

<400> SEQUENCE: 2

Tyr Met Phe Met
1

<210> SEQ ID NO 3
<211> LENGTH: 455
<212> TYPE: PRT
<213> ORGANISM: Homo sapiens
<220> FEATURE:
<221> NAME/KEY: MISC_FEATURE
<223> OTHER INFORMATION: mature human B7RP1

<400> SEQUENCE: 3

Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
            20                  25                  30

Tyr Val Tyr Trp Gln Thr Ser Glu Ser Lys Thr Val Val Thr Tyr His
        35                  40                  45
```

```
Ile Pro Gln Asn Ser Ser Leu Glu Asn Val Asp Ser Arg Tyr Arg Asn
 50                  55                  60
Arg Ala Leu Met Ser Pro Ala Gly Met Leu Arg Gly Asp Phe Ser Leu
 65                  70                  75                  80
Arg Leu Phe Asn Val Thr Pro Gln Asp Glu Gln Lys Phe His Cys Leu
                     85                  90                  95
Val Leu Ser Gln Ser Leu Gly Phe Gln Glu Val Leu Ser Val Glu Val
                100                 105                 110
Thr Leu His Val Ala Ala Asn Phe Ser Val Pro Val Val Ser Ala Pro
            115                 120                 125
His Ser Pro Ser Gln Asp Glu Leu Thr Phe Thr Cys Thr Ser Ile Asn
    130                 135                 140
Gly Tyr Pro Arg Pro Asn Val Tyr Trp Ile Asn Lys Thr Asp Asn Ser
145                 150                 155                 160
Leu Leu Asp Gln Ala Leu Gln Asn Asp Thr Val Phe Leu Asn Met Arg
                165                 170                 175
Gly Leu Tyr Asp Val Val Ser Val Leu Arg Ile Ala Arg Thr Pro Ser
                180                 185                 190
Val Asn Ile Gly Cys Cys Ile Glu Asn Val Leu Leu Gln Gln Asn Leu
            195                 200                 205
Thr Val Gly Ser Gln Thr Gly Asn Asp Ile Gly Glu Arg Asp Lys Ile
    210                 215                 220
Thr Glu Asn Pro Val Ser Thr Gly Glu Lys Asn Ala Ala Thr Trp Ser
225                 230                 235                 240
Ile Leu Ala Val Leu Cys Leu Leu Val Val Val Ala Val Ala Ile Gly
                245                 250                 255
Trp Val Cys Arg Asp Arg Cys Leu Gln His Ser Tyr Ala Gly Ala Trp
                260                 265                 270
Ala Val Ser Pro Glu Thr Glu Leu Thr Gly Glu Phe Ala Val Gly Ser
            275                 280                 285
Ser Arg Phe Trp Gly Ala Gln Gly Arg Leu Gly Cys Gln Leu Ser Phe
    290                 295                 300
Arg Val Ser Lys Asn Phe Gln Lys Ala Lys Val Pro Cys Leu Glu Gln
305                 310                 315                 320
Leu Leu Phe Leu Glu Thr Gln Arg Ser Pro Arg Trp Cys Ala Trp His
                325                 330                 335
Phe Leu Gln Pro Pro Leu Gly Met Gly Trp His Pro Gly Val His Phe
                340                 345                 350
Val Thr Leu Arg Trp Asp Phe Pro Asn Met His Arg Ser Arg Glu Thr
            355                 360                 365
Ser Ala Arg Pro Pro Arg Ser Pro Val Pro Ser Pro Asp Gln Gly Val
    370                 375                 380
Gln Gly Gly Ser Arg His Arg Arg Pro Ala Pro Met Gly Cys Pro Glu
385                 390                 395                 400
Trp Val Gln Ala Pro Ala Pro Ser Pro Arg Gly Val Ser Arg Ala Gly
                405                 410                 415
Pro Gly Thr Gly Ala Gln Pro Leu Trp Gly Val Arg Ser Gly Ser Gly
                420                 425                 430
His Arg Gln Leu Leu Ser Val Ala Ala Thr Pro Ala Ala Leu Val Cys
            435                 440                 445
Pro Ser Val Pro Gly Ala Thr
    450                 455
```

<210> SEQ ID NO 4
<211> LENGTH: 304
<212> TYPE: PRT
<213> ORGANISM: Homo sapiens
<220> FEATURE:
<221> NAME/KEY: MISC_FEATURE
<223> OTHER INFORMATION: mature human B7-2

<400> SEQUENCE: 4

Leu Lys Ile Gln Ala Tyr Phe Asn Glu Thr Ala Asp Leu Pro Cys Gln
1               5                   10                  15

Phe Ala Asn Ser Gln Asn Gln Ser Leu Ser Glu Leu Val Val Phe Trp
            20                  25                  30

Gln Asp Gln Glu Asn Leu Val Leu Asn Glu Val Tyr Leu Gly Lys Glu
        35                  40                  45

Lys Phe Asp Ser Val His Ser Lys Tyr Met Gly Arg Thr Ser Phe Asp
    50                  55                  60

Ser Asp Ser Trp Thr Leu Arg Leu His Asn Leu Gln Ile Lys Asp Lys
65                  70                  75                  80

Gly Leu Tyr Gln Cys Ile Ile His His Lys Lys Pro Thr Gly Met Ile
                85                  90                  95

Arg Ile His Gln Met Asn Ser Glu Leu Ser Val Leu Ala Asn Phe Ser
            100                 105                 110

Gln Pro Glu Ile Val Pro Ile Ser Asn Ile Thr Glu Asn Val Tyr Ile
        115                 120                 125

Asn Leu Thr Cys Ser Ser Ile His Gly Tyr Pro Glu Pro Lys Lys Met
    130                 135                 140

Ser Val Leu Leu Arg Thr Lys Asn Ser Thr Ile Glu Tyr Asp Gly Val
145                 150                 155                 160

Met Gln Lys Ser Gln Asp Asn Val Thr Glu Leu Tyr Asp Val Ser Ile
                165                 170                 175

Ser Leu Ser Val Ser Phe Pro Asp Val Thr Ser Asn Met Thr Ile Phe
            180                 185                 190

Cys Ile Leu Glu Thr Asp Lys Thr Arg Leu Leu Ser Ser Pro Phe Ser
        195                 200                 205

Ile Glu Leu Glu Asp Pro Gln Pro Pro Pro Asp His Ile Pro Trp Ile
    210                 215                 220

Thr Ala Val Leu Pro Thr Val Ile Ile Cys Val Met Val Phe Cys Leu
225                 230                 235                 240

Ile Leu Trp Lys Trp Lys Lys Lys Arg Pro Arg Asn Ser Tyr Lys
                245                 250                 255

Cys Gly Thr Asn Thr Met Glu Arg Glu Glu Ser Glu Gln Thr Lys Lys
            260                 265                 270

Arg Glu Lys Ile His Ile Pro Glu Arg Ser Asp Glu Ala Gln Arg Val
        275                 280                 285

Phe Lys Ser Ser Lys Thr Ser Ser Cys Asp Lys Ser Asp Thr Cys Phe
    290                 295                 300

<210> SEQ ID NO 5
<211> LENGTH: 179
<212> TYPE: PRT
<213> ORGANISM: Homo sapiens
<220> FEATURE:
<221> NAME/KEY: MISC_FEATURE
<223> OTHER INFORMATION: mature human ICOS

<400> SEQUENCE: 5

```
Glu Ile Asn Gly Ser Ala Asn Tyr Glu Met Phe Ile Phe His Asn Gly
1               5                   10                  15

Gly Val Gln Ile Leu Cys Lys Tyr Pro Asp Ile Val Gln Gln Phe Lys
            20                  25                  30

Met Gln Leu Leu Lys Gly Gly Gln Ile Leu Cys Asp Leu Thr Lys Thr
            35                  40                  45

Lys Gly Ser Gly Asn Thr Val Ser Ile Lys Ser Leu Lys Phe Cys His
        50                  55                  60

Ser Gln Leu Ser Asn Asn Ser Val Ser Phe Phe Leu Tyr Asn Leu Asp
65                  70                  75                  80

His Ser His Ala Asn Tyr Tyr Phe Cys Asn Leu Ser Ile Phe Asp Pro
                85                  90                  95

Pro Phe Lys Val Thr Leu Thr Gly Gly Tyr Leu His Ile Tyr Glu
            100                 105                 110

Ser Gln Leu Cys Cys Gln Leu Lys Phe Trp Leu Pro Ile Gly Cys Ala
                115                 120                 125

Ala Phe Val Val Val Cys Ile Leu Gly Cys Ile Leu Ile Cys Trp Leu
            130                 135                 140

Thr Lys Lys Lys Tyr Ser Ser Ser Val His Asp Pro Asn Gly Glu Tyr
145                 150                 155                 160

Met Phe Met Arg Ala Val Asn Thr Ala Lys Lys Ser Arg Leu Thr Asp
                165                 170                 175

Val Thr Leu

<210> SEQ ID NO 6
<211> LENGTH: 202
<212> TYPE: PRT
<213> ORGANISM: Homo sapiens
<220> FEATURE:
<221> NAME/KEY: MISC_FEATURE
<223> OTHER INFORMATION: mature human CD28

<400> SEQUENCE: 6

Asn Lys Ile Leu Val Lys Gln Ser Pro Met Leu Val Ala Tyr Asp Asn
1               5                   10                  15

Ala Val Asn Leu Ser Cys Lys Tyr Ser Tyr Asn Leu Phe Ser Arg Glu
            20                  25                  30

Phe Arg Ala Ser Leu His Lys Gly Leu Asp Ser Ala Val Glu Val Cys
            35                  40                  45

Val Val Tyr Gly Asn Tyr Ser Gln Gln Leu Gln Val Tyr Ser Lys Thr
        50                  55                  60

Gly Phe Asn Cys Asp Gly Lys Leu Gly Asn Glu Ser Val Thr Phe Tyr
65                  70                  75                  80

Leu Gln Asn Leu Tyr Val Asn Gln Thr Asp Ile Tyr Phe Cys Lys Ile
                85                  90                  95

Glu Val Met Tyr Pro Pro Pro Tyr Leu Asp Asn Glu Lys Ser Asn Gly
            100                 105                 110

Thr Ile Ile His Val Lys Gly Lys His Leu Cys Pro Ser Pro Leu Phe
            115                 120                 125

Pro Gly Pro Ser Lys Pro Phe Trp Val Leu Val Val Val Gly Gly Val
            130                 135                 140

Leu Ala Cys Tyr Ser Leu Leu Val Thr Val Ala Phe Ile Ile Phe Trp
145                 150                 155                 160

Val Arg Ser Lys Arg Ser Arg Leu Leu His Ser Asp Tyr Met Asn Met
                165                 170                 175
```

```
Thr Pro Arg Arg Pro Gly Pro Thr Arg Lys His Tyr Gln Pro Tyr Ala
            180                 185                 190

Pro Pro Arg Asp Phe Ala Ala Tyr Arg Ser
        195                 200

<210> SEQ ID NO 7
<211> LENGTH: 254
<212> TYPE: PRT
<213> ORGANISM: Homo sapiens
<220> FEATURE:
<221> NAME/KEY: MISC_FEATURE
<223> OTHER INFORMATION: mature human B7-1

<400> SEQUENCE: 7

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

Leu Leu Pro Ser Trp Ala Ile Thr Leu Ile Ser Val Asn Gly Ile Phe
210                 215                 220

Val Ile Cys Cys Leu Thr Tyr Cys Phe Ala Pro Arg Cys Arg Glu Arg
225                 230                 235                 240

Arg Arg Asn Glu Arg Leu Arg Arg Glu Ser Val Arg Pro Val
                245                 250

<210> SEQ ID NO 8
<211> LENGTH: 143
<212> TYPE: PRT
<213> ORGANISM: Homo sapiens
<220> FEATURE:
<221> NAME/KEY: MISC_FEATURE
<223> OTHER INFORMATION: mature human CD3 xi

<400> SEQUENCE: 8

Gln Ser Phe Gly Leu Leu Asp Pro Lys Leu Cys Tyr Leu Leu Asp Gly
1               5                   10                  15
```

```
Ile Leu Phe Ile Tyr Gly Val Ile Leu Thr Ala Leu Phe Leu Arg Val
             20                  25                  30

Lys Phe Ser Arg Ser Ala Asp Ala Pro Ala Tyr Gln Gln Gly Gln Asn
         35                  40                  45

Gln Leu Tyr Asn Glu Leu Asn Leu Gly Arg Arg Glu Glu Tyr Asp Val
     50                  55                  60

Leu Asp Lys Arg Arg Gly Arg Asp Pro Glu Met Gly Gly Lys Pro Gln
 65                  70                  75                  80

Arg Arg Lys Asn Pro Gln Glu Gly Leu Tyr Asn Glu Leu Gln Lys Asp
                 85                  90                  95

Lys Met Ala Glu Ala Tyr Ser Glu Ile Gly Met Lys Gly Glu Arg Arg
            100                 105                 110

Arg Gly Lys Gly His Asp Gly Leu Tyr Gln Gly Leu Ser Thr Ala Thr
        115                 120                 125

Lys Asp Thr Tyr Asp Ala Leu His Met Gln Ala Leu Pro Pro Arg
    130                 135                 140
```

<210> SEQ ID NO 9
<211> LENGTH: 185
<212> TYPE: PRT
<213> ORGANISM: Homo sapiens
<220> FEATURE:
<221> NAME/KEY: MISC_FEATURE
<223> OTHER INFORMATION: mature human CD3 epsilon

<400> SEQUENCE: 9

```
Asp Gly Asn Glu Glu Met Gly Gly Ile Thr Gln Thr Pro Tyr Lys Val
  1               5                  10                  15

Ser Ile Ser Gly Thr Thr Val Ile Leu Thr Cys Pro Gln Tyr Pro Gly
             20                  25                  30

Ser Glu Ile Leu Trp Gln His Asn Asp Lys Asn Ile Gly Gly Asp Glu
         35                  40                  45

Asp Asp Lys Asn Ile Gly Ser Asp Glu Asp His Leu Ser Leu Lys Glu
     50                  55                  60

Phe Ser Glu Leu Glu Gln Ser Gly Tyr Tyr Val Cys Tyr Pro Arg Gly
 65                  70                  75                  80

Ser Lys Pro Glu Asp Ala Asn Phe Tyr Leu Tyr Leu Arg Ala Arg Val
                 85                  90                  95

Cys Glu Asn Cys Met Glu Met Asp Val Met Ser Val Ala Thr Ile Val
            100                 105                 110

Ile Val Asp Ile Cys Ile Thr Gly Gly Leu Leu Leu Leu Val Tyr Tyr
        115                 120                 125

Trp Ser Lys Asn Arg Lys Ala Lys Ala Lys Pro Val Thr Arg Gly Ala
    130                 135                 140

Gly Ala Gly Gly Arg Gln Arg Gly Gln Asn Lys Glu Arg Pro Pro Pro
145                 150                 155                 160

Val Pro Asn Pro Asp Tyr Glu Pro Ile Arg Lys Gly Gln Arg Asp Leu
                165                 170                 175

Tyr Ser Gly Leu Asn Gln Arg Arg Ile
                180                 185
```

<210> SEQ ID NO 10
<211> LENGTH: 160
<212> TYPE: PRT
<213> ORGANISM: Homo sapiens
<220> FEATURE:
<221> NAME/KEY: MISC_FEATURE
<223> OTHER INFORMATION: mature human CD3 gamma

<400> SEQUENCE: 10

Gln Ser Ile Lys Gly Asn His Leu Val Lys Val Tyr Asp Tyr Gln Glu
1               5                   10                  15

Asp Gly Ser Val Leu Leu Thr Cys Asp Ala Glu Ala Lys Asn Ile Thr
            20                  25                  30

Trp Phe Lys Asp Gly Lys Met Ile Gly Phe Leu Thr Glu Asp Lys Lys
        35                  40                  45

Lys Trp Asn Leu Gly Ser Asn Ala Lys Asp Pro Arg Gly Met Tyr Gln
    50                  55                  60

Cys Lys Gly Ser Gln Asn Lys Ser Lys Pro Leu Gln Val Tyr Tyr Arg
65                  70                  75                  80

Met Cys Gln Asn Cys Ile Glu Leu Asn Ala Ala Thr Ile Ser Gly Phe
                85                  90                  95

Leu Phe Ala Glu Ile Val Ser Ile Phe Val Leu Ala Val Gly Val Tyr
            100                 105                 110

Phe Ile Ala Gly Gln Asp Gly Val Arg Gln Ser Arg Ala Ser Asp Lys
        115                 120                 125

Gln Thr Leu Leu Pro Asn Asp Gln Leu Tyr Gln Pro Leu Lys Asp Arg
    130                 135                 140

Glu Asp Asp Gln Tyr Ser His Leu Gln Gly Asn Gln Leu Arg Arg Asn
145                 150                 155                 160

<210> SEQ ID NO 11
<211> LENGTH: 150
<212> TYPE: PRT
<213> ORGANISM: Homo sapiens
<220> FEATURE:
<221> NAME/KEY: MISC_FEATURE
<223> OTHER INFORMATION: mature human CD3 sigma

<400> SEQUENCE: 11

Phe Lys Ile Pro Ile Glu Glu Leu Glu Asp Arg Val Phe Val Asn Cys
1               5                   10                  15

Asn Thr Ser Ile Thr Trp Val Glu Gly Thr Val Gly Thr Leu Leu Ser
            20                  25                  30

Asp Ile Thr Arg Leu Asp Leu Gly Lys Arg Ile Leu Asp Pro Arg Gly
        35                  40                  45

Ile Tyr Arg Cys Asn Gly Thr Asp Ile Tyr Lys Asp Lys Glu Ser Thr
    50                  55                  60

Val Gln Val His Tyr Arg Met Cys Gln Ser Cys Val Glu Leu Asp Pro
65                  70                  75                  80

Ala Thr Val Ala Gly Ile Ile Val Thr Asp Val Ile Ala Thr Leu Leu
                85                  90                  95

Leu Ala Leu Gly Val Phe Cys Phe Ala Gly His Glu Thr Gly Arg Leu
            100                 105                 110

Ser Gly Ala Ala Asp Thr Gln Ala Leu Leu Arg Asn Asp Gln Val Tyr
        115                 120                 125

Gln Pro Leu Arg Asp Arg Asp Asp Ala Gln Tyr Ser His Leu Gly Gly
    130                 135                 140

Asn Trp Ala Arg Asn Lys
145                 150

<210> SEQ ID NO 12
<211> LENGTH: 283
<212> TYPE: PRT
<213> ORGANISM: Homo sapiens
<220> FEATURE:
<221> NAME/KEY: MISC_FEATURE
<223> OTHER INFORMATION: mature ICOS-CD3 fusion protein (ICOS-CD3 III)

<400> SEQUENCE: 12

Glu Ile Asn Gly Ser Ala Asn Tyr Glu Met Phe Ile Phe His Asn Gly
1               5                   10                  15
Gly Val Gln Ile Leu Cys Lys Tyr Pro Asp Ile Val Gln Gln Phe Lys
            20                  25                  30
Met Gln Leu Leu Lys Gly Gly Gln Ile Leu Cys Asp Leu Thr Lys Thr
        35                  40                  45
Lys Gly Ser Gly Asn Thr Val Ser Ile Lys Ser Leu Lys Phe Cys His
    50                  55                  60
Ser Gln Leu Ser Asn Asn Ser Val Ser Phe Phe Leu Tyr Asn Leu Asp
65                  70                  75                  80
His Ser His Ala Asn Tyr Tyr Phe Cys Asn Leu Ser Ile Phe Asp Pro
                85                  90                  95
Pro Pro Phe Lys Val Thr Leu Thr Gly Gly Tyr Leu His Ile Tyr Glu
            100                 105                 110
Ser Gln Leu Cys Cys Gln Leu Lys Phe Trp Leu Pro Ile Gly Cys Ala
        115                 120                 125
Ala Phe Val Val Val Cys Ile Leu Gly Cys Ile Leu Ile Cys Trp Leu
    130                 135                 140
Thr Lys Lys Lys Tyr Ser Ser Ser Val His Asp Pro Asn Gly Glu Tyr
145                 150                 155                 160
Met Phe Met Arg Ala Val Asn Thr Ala Lys Lys Ser Arg Leu Thr Asp
                165                 170                 175
Val Thr Leu Ala Pro Ala Tyr Gln Gln Gly Gln Asn Gln Leu Tyr Asn
            180                 185                 190
Glu Leu Asn Leu Gly Arg Arg Glu Glu Tyr Asp Val Leu Asp Lys Arg
        195                 200                 205
Arg Gly Arg Asp Pro Glu Met Gly Gly Lys Pro Gln Arg Arg Lys Asn
    210                 215                 220
Pro Gln Glu Gly Leu Tyr Asn Glu Leu Gln Lys Asp Lys Met Ala Glu
225                 230                 235                 240
Ala Tyr Ser Glu Ile Gly Met Lys Gly Glu Arg Arg Arg Gly Lys Gly
                245                 250                 255
His Asp Gly Leu Tyr Gln Gly Leu Ser Thr Ala Thr Lys Asp Thr Tyr
            260                 265                 270
Asp Ala Leu His Met Gln Ala Leu Pro Pro Arg
        275                 280

<210> SEQ ID NO 13
<211> LENGTH: 849
<212> TYPE: DNA
<213> ORGANISM: Homo sapiens
<220> FEATURE:
<221> NAME/KEY: misc_feature
<223> OTHER INFORMATION: amino acid sequence of SEQ ID NO:12

<400> SEQUENCE: 13
gaaatcaatg gttctgccaa ttatgagatg tttatatttc acaacggagg tgtacaaatt      60
ttatgcaaat atcctgacat tgtccagcaa tttaaaatgc agttgctgaa agggggcaa      120 atactctgcg atctcactaa gacaaaagga agtggaaaca cagtgtccat taagagtctg     180
aaattctgcc attctcagtt atccaacaac agtgtgtctct ttttttctata caacttggac    240

-continued

```
cattctcatg ccaactatta cttctgcaac ctatcaattt ttgatcctcc tccttttaaa     300
gtaactctta caggaggata tttgcatatt tatgaatcac aactttgttg ccagctgaag     360
ttctggttac ccataggatg tgcagccttt gttgtagtct gcattttggg atgcatactt     420
atttgttggc ttacaaaaaa gaagtattca tccagtgtgc acgaccctaa cggtgaatac     480
atgttcatga gagcagtgaa cacagccaaa aaatctagac tcacagatgt gaccctagct     540
cctgcgtacc agcaggggca gaatcaactc tataatgaac ttaacctggg tcggcgggag     600
gaatacgatg tgttggacaa agaagaggc cgggacccag agatgggcgg caaaccccag     660
cggagaaaga atccccagga gggactctat aatgaattgc aaaagacaa gatggcagag     720 gcttattccg agataggtat gaaggggaa cggaggcggg gcaagggca cgatggcctt     780 tatcagggat tgtctacagc cacaaaagac acgtacgacg ctctgcatat gcaggcactg     840
ccccctaga                                                             849
```

<210> SEQ ID NO 14
<211> LENGTH: 288
<212> TYPE: PRT
<213> ORGANISM: Homo sapiens
<220> FEATURE:
<221> NAME/KEY: MISC_FEATURE
<223> OTHER INFORMATION: mature ICOS-CD3 fusion protein (ICOS-CD3 II)

<400> SEQUENCE: 14

```
Glu Ile Asn Gly Ser Ala Asn Tyr Glu Met Phe Ile Phe His Asn Gly
1               5                  10                  15

Gly Val Gln Ile Leu Cys Lys Tyr Pro Asp Ile Val Gln Gln Phe Lys
            20                  25                  30

Met Gln Leu Leu Lys Gly Gly Gln Ile Leu Cys Asp Leu Thr Lys Thr
        35                  40                  45

Lys Gly Ser Gly Asn Thr Val Ser Ile Lys Ser Leu Lys Phe Cys His
    50                  55                  60

Ser Gln Leu Ser Asn Asn Ser Val Ser Phe Phe Leu Tyr Asn Leu Asp
65                  70                  75                  80

His Ser His Ala Asn Tyr Tyr Phe Cys Asn Leu Ser Ile Phe Asp Pro
                85                  90                  95

Pro Pro Phe Lys Val Thr Leu Thr Gly Gly Tyr Leu His Ile Tyr Glu
            100                 105                 110

Ser Gln Leu Cys Cys Gln Leu Lys Phe Trp Leu Pro Ile Gly Cys Ala
        115                 120                 125

Ala Phe Val Val Val Cys Ile Leu Gly Cys Ile Leu Ile Cys Trp Leu
    130                 135                 140

Thr Lys Lys Lys Tyr Ser Ser Ser Val His Asp Pro Asn Gly Glu Tyr
145                 150                 155                 160

Met Phe Met Arg Ala Val Asn Thr Ala Lys Lys Ser Arg Leu Thr Asp
                165                 170                 175

Val Thr Leu Ser Arg Ser Ala Asp Ala Pro Ala Tyr Gln Gln Gly Gln
            180                 185                 190

Asn Gln Leu Tyr Asn Glu Leu Asn Leu Gly Arg Arg Glu Glu Tyr Asp
        195                 200                 205

Val Leu Asp Lys Arg Arg Gly Arg Asp Pro Glu Met Gly Gly Lys Pro
    210                 215                 220

Gln Arg Arg Lys Asn Pro Gln Glu Gly Leu Tyr Asn Glu Leu Gln Lys
225                 230                 235                 240

Asp Lys Met Ala Glu Ala Tyr Ser Glu Ile Gly Met Lys Gly Glu Arg
```

```
                245                 250                 255
Arg Arg Gly Lys Gly His Asp Gly Leu Tyr Gln Gly Leu Ser Thr Ala
            260                 265                 270

Thr Lys Asp Thr Tyr Asp Ala Leu His Met Gln Ala Leu Pro Pro Arg
            275                 280                 285
```

<210> SEQ ID NO 15
<211> LENGTH: 864
<212> TYPE: DNA
<213> ORGANISM: Homo sapiens
<220> FEATURE:
<221> NAME/KEY: misc_feature
<223> OTHER INFORMATION: amino acid sequence of SEQ ID NO:14

<400> SEQUENCE: 15

```
gaaatcaatg gttctgccaa ttatgagatg tttatatttc acaacggagg tgtacaaatt    60
ttatgcaaat atcctgacat tgtccagcaa tttaaaatgc agttgctgaa agggggcaa    120
atactctgcg atctcactaa gacaaaagga agtggaaaca cagtgtccat taagagtctg    180
aaattctgcc attctcagtt atccaacaac agtgtctctt ttttctata caacttggac    240
cattctcatg ccaactatta cttctgcaac ctatcaattt tgatcctcc tcctttttaaa    300
gtaactctta caggaggata tttgcatatt tatgaatcac aactttgttg ccagctgaag    360
ttctggttac ccataggatg tgcagccttt gttgtagtct gcattttggg atgcatactt    420
atttgttggc ttacaaaaaa gaagtattca tccagtgtgc acgaccctaa cggtgaatac    480
atgttcatga gagcagtgaa cacagccaaa aaatctagac tcacagatgt gacccctaagt    540
cgctccgccg acgctcctgc gtaccagcag gggcagaatc aactctataa tgaacttaac    600
ctgggtcggc gggaggaata cgatgtgttg gacaaaagaa gaggccggga cccagagatg    660
ggcggcaaac cccagcggag aaagaatccc caggagggac tctataatga attgcaaaaa    720
gacaagatgg cagaggctta ttccgagata ggtatgaaag gggaacggag gcggggcaaa    780
gggcacgatg gcctttatca gggattgtct acagccacaa aagacacgta cgacgctctg    840
catatgcagg cactgccccc taga                                          864
```

<210> SEQ ID NO 16
<211> LENGTH: 292
<212> TYPE: PRT
<213> ORGANISM: Homo sapiens
<220> FEATURE:
<221> NAME/KEY: MISC_FEATURE
<223> OTHER INFORMATION: mature ICOS-CD3 fusion protein (ICOS-CD3 I)

<400> SEQUENCE: 16

```
Glu Ile Asn Gly Ser Ala Asn Tyr Glu Met Phe Ile Phe His Asn Gly
1               5                   10                  15

Gly Val Gln Ile Leu Cys Lys Tyr Pro Asp Ile Val Gln Gln Phe Lys
            20                  25                  30

Met Gln Leu Leu Lys Gly Gly Gln Ile Leu Cys Asp Leu Thr Lys Thr
        35                  40                  45

Lys Gly Ser Gly Asn Thr Val Ser Ile Lys Ser Leu Lys Phe Cys His
    50                  55                  60

Ser Gln Leu Ser Asn Asn Ser Val Ser Phe Phe Leu Tyr Asn Leu Asp
65                  70                  75                  80

His Ser His Ala Asn Tyr Tyr Phe Cys Asn Leu Ser Ile Phe Asp Pro
                85                  90                  95

Pro Pro Phe Lys Val Thr Leu Thr Gly Gly Tyr Leu His Ile Tyr Glu
```

```
                100             105                 110
        Ser Gln Leu Cys Cys Gln Leu Lys Phe Trp Leu Pro Ile Gly Cys Ala
            115                 120                 125

Ala Phe Val Val Cys Ile Leu Gly Cys Ile Leu Ile Cys Trp Leu
            130                 135                 140

Thr Lys Lys Lys Tyr Ser Ser Val His Asp Pro Asn Gly Glu Tyr
        145                 150                 155                 160

Met Phe Met Arg Ala Val Asn Thr Ala Lys Lys Ser Arg Leu Thr Asp
                        165                 170                 175

Val Thr Leu Arg Val Lys Phe Ser Arg Ser Ala Asp Ala Pro Ala Tyr
                        180                 185                 190

Gln Gln Gly Gln Asn Gln Leu Tyr Asn Glu Leu Asn Leu Gly Arg Arg
                        195                 200                 205

Glu Glu Tyr Asp Val Leu Asp Lys Arg Arg Gly Arg Asp Pro Glu Met
            210                 215                 220

Gly Gly Lys Pro Gln Arg Arg Lys Asn Pro Gln Glu Gly Leu Tyr Asn
        225                 230                 235                 240

Glu Leu Gln Lys Asp Lys Met Ala Glu Ala Tyr Ser Glu Ile Gly Met
                        245                 250                 255

Lys Gly Glu Arg Arg Arg Gly Lys Gly His Asp Gly Leu Tyr Gln Gly
                        260                 265                 270

Leu Ser Thr Ala Thr Lys Asp Thr Tyr Asp Ala Leu His Met Gln Ala
                        275                 280                 285

Leu Pro Pro Arg
            290

<210> SEQ ID NO 17
<211> LENGTH: 876
<212> TYPE: DNA
<213> ORGANISM: Homo sapiens
<220> FEATURE:
<221> NAME/KEY: misc_feature
<223> OTHER INFORMATION: amino acid sequence of SEQ ID NO:16

<400> SEQUENCE: 17
gaaatcaatg gttctgccaa ttatgagatg tttatatttc acaacggagg tgtacaaatt     60
ttatgcaaat atcctgacat tgtccagcaa tttaaaatgc agttgctgaa aggggggcaa    120
atactctgcg atctcactaa gacaaaagga agtggaaaca cagtgtccat taagagtctg    180
aaattctgcc attctcagtt atccaacaac agtgtctctt tttttctata caacttggac    240
cattctcatg ccaactatta cttctgcaac ctatcaattt tgatcctcc tccttttaaa    300 gtaactctta caggaggata tttgcatatt tatgaatcac aactttgttg ccagctgaag    360
ttctggttac ccataggatg tgcagccttt gttgtagtct gcattttggg atgcatactt    420
atttgttggc ttacaaaaaa gaagtattca tccagtgtgc acgaccctaa cggtgaatac    480
atgttcatga gagcagtgaa cacagccaaa aaatctagac tcacagatgt gaccctacgc    540
gtgaagttca gtcgctccgc cgacgctcct gcgtaccagc aggggcagaa tcaactctat    600
aatgaactta acctgggtcg gcgggaggaa tacgatgtgt tggacaaaag aagaggccgg    660
gacccagaga tgggcggcaa accccagcgg agaaagaatc cccaggaggg actctataat    720
gaattgcaaa aagacaagat ggcagaggct tattccgaga taggtatgaa aggggaacgg    780
aggcggggca aagggcacga tggcctttat cagggattgt ctacagccac aaaagacacg    840
tacgacgctc tgcatatgca ggcactgccc cctaga                              876
```

<210> SEQ ID NO 18
<211> LENGTH: 180
<212> TYPE: PRT
<213> ORGANISM: Mus musculus
<220> FEATURE:
<221> NAME/KEY: MISC_FEATURE
<223> OTHER INFORMATION: mature murine ICOS

<400> SEQUENCE: 18

Glu Ile Asn Gly Ser Ala Asp His Arg Met Phe Ser Phe His Asn Gly
1               5                   10                  15

Gly Val Gln Ile Ser Cys Lys Tyr Pro Glu Thr Val Gln Gln Leu Lys
            20                  25                  30

Met Arg Leu Phe Arg Glu Arg Glu Val Leu Cys Glu Leu Thr Lys Thr
        35                  40                  45

Lys Gly Ser Gly Asn Ala Val Ser Ile Lys Asn Pro Met Leu Cys Leu
    50                  55                  60

Tyr His Leu Ser Asn Asn Ser Val Ser Phe Phe Leu Asn Asn Pro Asp
65                  70                  75                  80

Ser Ser Gln Gly Ser Tyr Tyr Phe Cys Ser Leu Ser Ile Phe Asp Pro
                85                  90                  95

Pro Pro Phe Gln Glu Arg Asn Leu Ser Gly Gly Tyr Leu His Ile Tyr
            100                 105                 110

Glu Ser Gln Leu Cys Cys Gln Leu Lys Leu Trp Leu Pro Val Gly Cys
        115                 120                 125

Ala Ala Phe Val Val Leu Leu Phe Gly Cys Ile Leu Ile Ile Trp
    130                 135                 140

Phe Ser Lys Lys Lys Tyr Gly Ser Ser Val His Asp Pro Asn Ser Glu
145                 150                 155                 160

Tyr Met Phe Met Ala Ala Val Asn Thr Asn Lys Lys Ser Arg Leu Ala
                165                 170                 175

Gly Val Thr Ser
            180

<210> SEQ ID NO 19
<211> LENGTH: 198
<212> TYPE: PRT
<213> ORGANISM: Mus musculus
<220> FEATURE:
<221> NAME/KEY: misc_feature
<223> OTHER INFORMATION: mature murine CD28

<400> SEQUENCE: 19

Lys Ile Leu Val Lys Gln Ser Pro Leu Leu Val Val Asp Ser Asn Glu
1               5                   10                  15

Val Ser Leu Ser Cys Arg Tyr Ser Tyr Asn Leu Leu Ala Lys Glu Phe
            20                  25                  30

Arg Ala Ser Leu Tyr Lys Gly Val Asn Ser Asp Val Glu Val Cys Val
        35                  40                  45

Gly Asn Gly Asn Phe Thr Tyr Gln Pro Gln Phe Arg Ser Asn Ala Glu
    50                  55                  60

Phe Asn Cys Asp Gly Asp Phe Asp Asn Glu Thr Val Thr Phe Arg Leu
65                  70                  75                  80

Trp Asn Leu His Val Asn His Thr Asp Ile Tyr Phe Cys Lys Ile Glu
                85                  90                  95

Phe Met Tyr Pro Pro Pro Tyr Leu Asp Asn Glu Arg Ser Asn Gly Thr
            100                 105                 110

```
Ile Ile His Ile Lys Glu Lys His Leu Cys His Thr Gln Ser Ser Pro
            115                 120                 125

Lys Leu Phe Trp Ala Leu Val Val Ala Gly Val Leu Phe Cys Tyr
        130             135             140

Gly Leu Val Thr Val Ala Leu Cys Val Ile Trp Thr Asn Ser Arg
145             150             155                     160

Arg Asn Arg Leu Leu Gln Ser Asp Tyr Met Asn Met Thr Pro Arg Arg
                165             170             175

Pro Gly Leu Thr Arg Lys Pro Tyr Gln Pro Tyr Ala Pro Ala Arg Asp
            180             185             190

Phe Ala Ala Tyr Arg Pro
        195

<210> SEQ ID NO 20
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 20

Tyr Val Lys Met
1

<210> SEQ ID NO 21
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 21

Thr Glu Tyr Ala Thr Ile
1               5
```